US011547649B2

(12) United States Patent
Baek et al.

(10) Patent No.: US 11,547,649 B2
(45) Date of Patent: Jan. 10, 2023

(54) FUSION PROTEIN BOUND TO CELL-PERMEABLE PEPTIDE, AND COMPOSITION COMPRISING FUSION PROTEIN OR CELL-PERMEABLE PEPTIDE AND EPITHELIAL CELL GROWTH FACTOR AS ACTIVE INGREDIENTS

(71) Applicant: Avixgen Inc., Seoul (KR)

(72) Inventors: Yi Yong Baek, Gyeonggi-do (KR); Woo Ri Shin, Incheon (KR); Si Eun Park, Seoul (KR); Jun Sub Choi, Gyeonggi-do (KR); Hye Cheong Koo, Gyeonggi-do (KR)

(73) Assignee: AVIXGEN INC., Seoul (KR)

( * ) Notice: Subject to any disclaimer, the term of this patent is extended or adjusted under 35 U.S.C. 154(b) by 0 days.

(21) Appl. No.: 17/251,454

(22) PCT Filed: Jun. 7, 2019

(86) PCT No.: PCT/KR2019/006848
§ 371 (c)(1),
(2) Date: Dec. 11, 2020

(87) PCT Pub. No.: WO2019/240430
PCT Pub. Date: Dec. 19, 2019

(65) Prior Publication Data
US 2021/0251872 A1 Aug. 19, 2021

(30) Foreign Application Priority Data
Jun. 14, 2018 (KR) .................. 10-2018-0068378

(51) Int. Cl.
| | | |
|---|---|---|
| A61K 8/64 | (2006.01) | |
| A61Q 19/08 | (2006.01) | |
| C07K 1/14 | (2006.01) | |
| C07K 14/485 | (2006.01) | |
| C07K 7/06 | (2006.01) | |
| C12N 9/52 | (2006.01) | |
| A61K 38/00 | (2006.01) | |

(52) U.S. Cl.
CPC .............. *A61K 8/64* (2013.01); *A61Q 19/08* (2013.01); *C07K 1/14* (2013.01); *C07K 7/06* (2013.01); *C07K 14/485* (2013.01); *C12N 9/52* (2013.01); *A61K 38/00* (2013.01); *C07K 2319/10* (2013.01); *C12Y 304/24069* (2013.01)

(58) Field of Classification Search
CPC .......... A61K 38/00; A61K 8/64; A61Q 19/08; C07K 14/33; C07K 14/485; C07K 1/14; C07K 2319/01; C07K 2319/10; C07K 7/06; C12N 9/52; C12Y 304/24069
See application file for complete search history.

(56) References Cited

U.S. PATENT DOCUMENTS

| | | |
|---|---|---|
| 2015/0133379 A1 | 5/2015 | Lee et al. |
| 2015/0266939 A1 | 9/2015 | Vogan et al. |

FOREIGN PATENT DOCUMENTS

| | | |
|---|---|---|
| CN | 1765929 | 5/2006 |
| KR | 10-1135460 | 6/2012 |
| KR | 10-2015-0056022 | 5/2015 |
| KR | 10-1636846 | 7/2016 |
| KR | 10-2017-0002475 | 1/2017 |
| KR | 10-1813560 | 1/2018 |

OTHER PUBLICATIONS

James G. Omichinski, Structural characterization of a 39-residue synthetic peptide containing the two zinc binding domains from the HIV-1 p7 nucleocapsid protein by CD and NMR spectroscopy, vol. 292, No. 1, 2, 25-30 FEBS, 1991.*
Christine Voelkel, Protein transduction from retroviral Gag precursors, PNAS, Apr. 27, 2010, vol. 107, No. 17, pp. 7805-7810.*
Supplemental Flgues and Data, Christine Voelkel, Protein transduction from retroviral Gag precursors, PNAS, Apr. 27, 2010, vol. 107, No. 17, pp. 7805-7810.*
CN1765929a, google english Translation, accessed on Mar. 25, 2022.*
GenBank Accession No. BAA12996.1: Gag [Human immunodeficiency virus 1] (Jul. 21, 2016).
International Search Report, dated Sep. 16, 2019 in corresponding International Patent Application No. PCT/KR2019/006848.

* cited by examiner

*Primary Examiner* — Julie Ha
*Assistant Examiner* — Erinne R Dabkowski
(74) *Attorney, Agent, or Firm* — Wenderoth, Lind & Ponack, L.L.P.

(57) ABSTRACT

The present invention pertains to: a botulinum toxin, epithelial cell growth factor, or hexapeptide fusion protein bound to skin tissues and cell-permeable peptides, or an epithelial cell growth factor mixed with skin tissues and cell-permeable peptides; and a composition comprising same. The fusion protein or the epithelial cell growth factor mixed with cell-permeable peptides has increased cell permeability compared to protein by itself, and is thus useful for improving the condition of skin, treating wrinkles, relieving muscle tension, and treating wounds.

5 Claims, 14 Drawing Sheets

Specification includes a Sequence Listing.

1: cell only
2: BTLC 3μg
3: ACPBTLC 3μg
4: ACP2BTLC 3μg
5: ACP1BTLC 3μg

A

B

FUSION PROTEIN BOUND TO CELL-PERMEABLE PEPTIDE, AND COMPOSITION COMPRISING FUSION PROTEIN OR CELL-PERMEABLE PEPTIDE AND EPITHELIAL CELL GROWTH FACTOR AS ACTIVE INGREDIENTS

TECHNICAL FIELD

The present disclosure relates to a conjugate including a cell-penetrating peptide, and a composition including, as an active ingredient, either the conjugate or a cell-penetrating peptide and epidermal growth factor.

BACKGROUND ART

Skin is a tissue that is constantly in contact with the external environment. It functions as a protective barrier that prevents leakage of body fluid, infection and water loss. Especially, the stratum corneum of the epidermis, which is the outermost layer of the skin, prevents skin dryness by suppressing loss of water and electrolytes out of the skin and provides an environment for normal biochemical metabolism of the skin. In addition, it protects the human body from external physical damage and chemicals and plays an important role in preventing bacteria, fungi, viruses, etc. from invading the skin. However, with age, skin cells are damaged due to various pollutants, strong ultraviolet rays, stress, and subnutrition, and the cells do not properly proliferate, resulting in skin wrinkles, loss of skin elasticity, and keratinization of the skin.

Accordingly, the development of high-functional cosmetics that combines new technologies with cosmetic materials has been continuously made. In addition, with an increase in the number of consumers demanding specific effects such as whitening, wrinkle reduction, and skin regeneration, the value of functional cosmetics in the cosmetics industry has further increased, and studies have been focused to apply various materials to cosmetics.

Although it is known that low-molecular-weight synthetic compounds or natural compounds having a molecular weight of 500 Da or smaller, which are commonly used as cosmetic raw materials, are easily delivered into cells, the penetration efficiency of the low-molecular-weight substances is low due to the intrinsic properties of the stratum corneum constituting the skin barrier. It is more difficult for macromolecules with a molecular weight of 500 Da or larger, such as proteins, peptides and nucleic acids, to penetrate the cell membrane consisting of a lipid bilayer structure, due to their large molecular weight. As a method for improving the efficiency with which these low-molecular-weight substances and macromolecules pass through the plasma membrane of cells, transdermal drug delivery (TDD) has recently attracted a lot of attention. However, the biggest obstacles to the transdermal drug delivery are keratinocytes in the stratum corneum and intercorneocyte lipids. Most molecules exhibiting physiological activity in the skin (hereinafter, referred to as skin physiologically active molecules) have low transdermal permeability due to the resistance of the stratum corneum of the skin to these molecules.

A variety of methods capable of increasing the transdermal permeability of these skin physiologically active molecules have been studied. In recent years, delivery systems using cell-penetrating peptides have attracted a lot of attention. Cell-penetrating peptides (CPPs) are cell membrane-penetrating peptides, each consisting of a short peptide of about 10 to 60 amino acids, and are mostly derived from protein-transduction domains or membrane-translocating sequences. It is known that, unlike general intracellular transduction pathways of foreign substances, CPPs can move into cells without damaging the cell membrane, and can intracellularly deliver even DNAs or proteins known to not pass through the cell membrane.

The present inventors have found that peptides derived from the HIV (human immunodeficiency virus) nucleocapsid can increase the cell-permeability of skin physiologically active molecules, thereby completing the present disclosure.

DISCLOSURE

Technical Problem

It is an object of the present disclosure to provide a conjugate including a cell-penetrating peptide conjugated to botulinum toxin, epidermal growth factor or hexapeptide, which is a skin physiologically active molecule.

Another object of the present disclosure is to provide a cosmetic composition and a pharmaceutical composition for wrinkle reduction, muscle stiffness relief or skin wound healing, which include, as an active ingredient, either the conjugate or a mixture of epidermal growth factor, which is a skin physiologically active molecule, and a cell-penetrating peptide, a treatment method, and the use thereof.

Technical Solution

One aspect of the present disclosure provides a conjugate including: a skin physiologically active molecule; and a cell-penetrating peptide including the amino acid sequence selected from the group consisting of SEQ ID NOs: 1 to 3, wherein the skin physiologically active molecule is a polypeptide set forth in any one amino acid sequence selected from the group consisting of SEQ ID NOs: 4 to 6.

Another aspect of the present disclosure provides a polynucleotide encoding the conjugate.

Still another aspect of the present disclosure provides a recombinant vector including the polynucleotide.

Yet another aspect of the present disclosure provides a host cell including the recombinant vector.

Still yet another aspect of the present disclosure provides a method for producing a conjugate, the method including steps of: (a) culturing the host cell in a culture medium; and (b) recovering the conjugate from the culture medium.

A further aspect of the present disclosure provides a cosmetic composition for skin condition improvement including, as an active ingredient, either the conjugate or a cell-penetrating peptide consisting of the amino acid sequence of SEQ ID NO: 1 or SEQ ID NO: 2, and a polypeptide consisting of the amino acid sequence of SEQ ID NO: 5.

According to one embodiment of the present disclosure, the cosmetic composition may be a formulation selected from the group consisting of emulsion, cream, essence, skin lotion, liposomes, microcapsules, composite particles, shampoo, and rinse.

Another further aspect of the present disclosure provides a pharmaceutical composition for wrinkle reduction, muscle stiffness relief or skin wound healing, the pharmaceutical composition including, as an active ingredient, either the conjugate or a cell-penetrating peptide consisting of the amino acid sequence of SEQ ID NO: 1 or SEQ ID NO: 2, and a polypeptide consisting of the amino acid sequence of SEQ ID NO: 5.

Still another further aspect of the present disclosure provides a method for wrinkle reduction, muscle stiffness relief or skin wound healing, the method including a step of administering the composition to a subject.

Yet another further aspect of the present disclosure provides the use of either the conjugate or a cell-penetrating peptide consisting of the amino acid sequence of SEQ ID NO: 1 or SEQ ID NO: 2, and a polypeptide consisting of the amino acid sequence of SEQ ID NO: 5, in the manufacture of a medicament for wrinkle reduction, muscle stiffness relief or skin wound healing.

Advantageous Effects

A conjugate including a botulinum toxin, epidermal growth factor or hexapeptide conjugated to a skin tissue- and cell-penetrating peptide and, or a mixture of a cell-penetrating peptide and epidermal growth factor, has an increased ability to penetrate skin tissue and cells, compared to proteins alone, and thus may be useful for skin condition improvement and skin wound healing.

BRIEF DESCRIPTION OF DRAWINGS

FIG. 4A shows the results of staining with anti-His antibody, and FIG. 4B shows the results of staining with anti-Botox antibody.

FIG. 16A show the results obtained by a mixture of ACP and EGF, and FIG. 16B show the results obtained by a mixture of ACP2 and EGF.

BEST MODE

Figure 1:
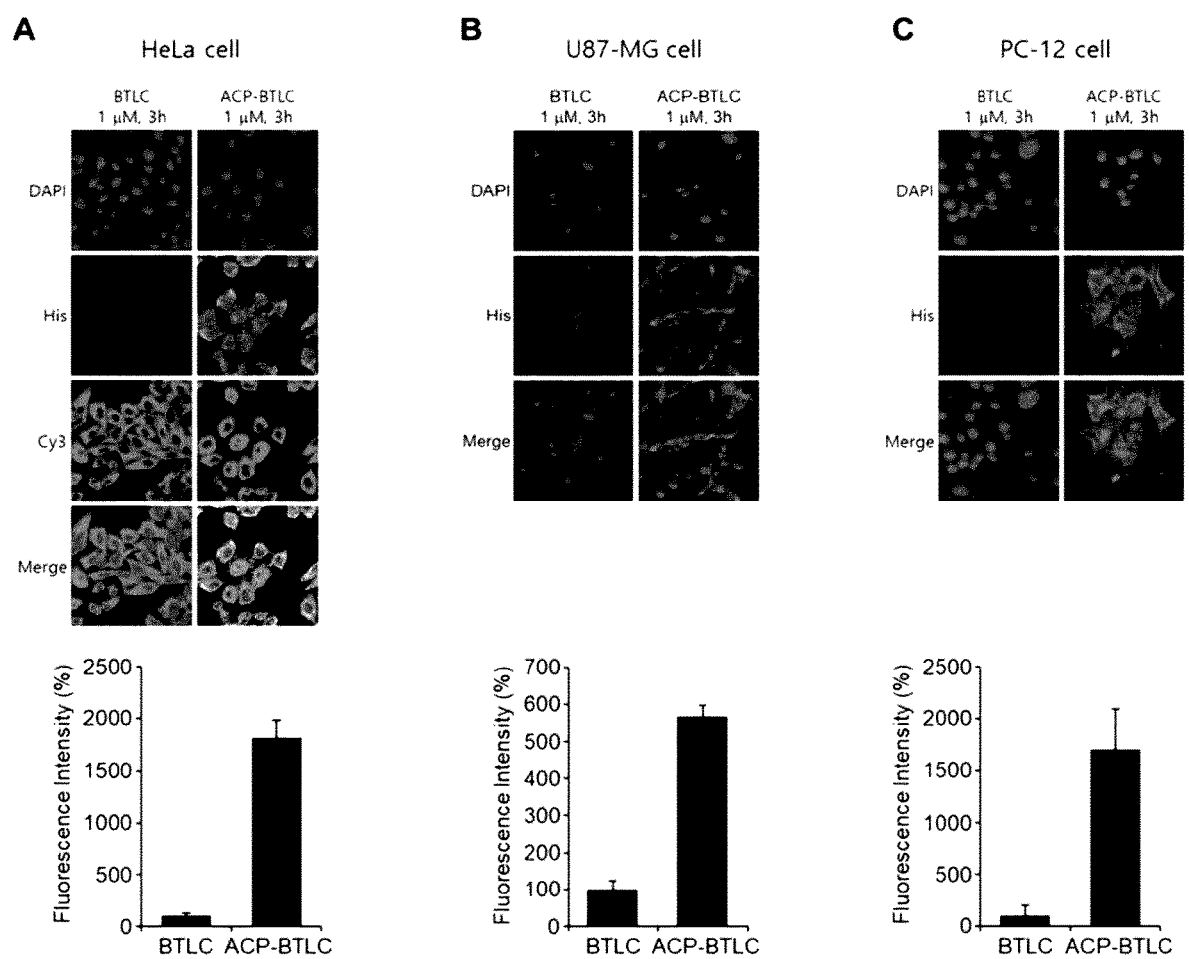
FIG. 1 shows the results of analyzing the cell membrane-penetrating activity of botulinum toxin (BTLC) and advanced cell penetrating peptide-botulinum toxin (ACP-BTLC) in HeLa cells (A), U87-MG cells (B) and PC-12 cells (C).

To achieve the above objects, one aspect of the present disclosure provides a conjugate including:
a skin physiologically active molecule; and
a cell-penetrating peptide including the amino acid sequence selected from the group consisting of SEQ ID NOs: 1 to 3,
wherein the skin physiologically active molecule is a polypeptide set forth in any one amino acid sequence selected from the group consisting of SEQ ID NOs: 4 to 6.

As used herein, the term "cell-penetrating peptide (CPP)" refers to a cell membrane-penetrating peptide consisting of a short peptide of about 10 to about 60 amino acids, which can move into a cell without damaging the cell membrane and can intracellularly deliver even a DNA or protein that cannot pass through the cell membrane.

As used herein, the term "conjugate" refers to a substance in which a cell-penetrating peptide and a biologically or pharmaceutically active substance are linked together by a chemical/physical covalent or non-covalent bond.

In one embodiment of the present disclosure, the expression "biologically or pharmaceutically active substance" capable of forming the conjugate by binding to the cell-penetrating peptide means a substance that can regulate physiological phenomena in vivo. The expression includes DNA, RNA, proteins, peptides, lipids, carbohydrates, chemical compounds, or fluorescent labels.

For example, as the protein, there may be used botulinum toxin (SEQ ID NO: 4), epidermal growth factor (SEQ ID NO: 5) or hexapeptide (SEQ ID NO: 6), which is a skin physiologically active molecule.

In one embodiment of the present disclosure, the conjugate may include the amino acid sequence selected from the group consisting of SEQ ID NOs: 7 to 12.

Another aspect of the present disclosure provides a polynucleotide encoding the conjugate.

As used herein, the term "polynucleotide" refers to a polymer of deoxyribonucleotide or ribonucleotide that exists in a single-stranded or double-stranded form. The term includes RNA genome sequences, DNAs (gDNA and cDNA), and RNA sequences transcribed therefrom, and includes analogues of natural polynucleotide, unless otherwise indicated.

In one embodiment of the present disclosure, the polynucleotide includes not only a nucleotide sequence encoding the conjugate, but also a sequence complementary thereto. The complementary sequences include not only completely complementary sequences, but also substantially complementary sequences. In addition, the polynucleotide sequence may be modified, and such modifications include addition, deletion or non-conservative substitution or conservative substitution of nucleotides.

In one embodiment of the present disclosure, the polynucleotide encoding the conjugate may include a polynucleotide selected from the group consisting of SEQ ID NOs: 19 to 24.

Still another aspect of the present disclosure provides a recombinant vector including the polynucleotide sequence encoding the conjugate.

As used herein, the term "vector" refers to a means for expressing a target gene in a host cell. Examples of the vector include, but are not limited to, plasmid vectors, cosmid vectors, and viral vectors such as bacteriophage vectors, adenoviral vectors, retroviral vectors and adeno-associated viral vectors. Vectors that may be used as the recombinant vector may be constructed by engineering plasmids (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19, etc.), phages (e.g., λgt4λB, λ-Charon, λΔz1, and M13, etc.), or viruses (e.g., CMV, SV40, etc.), which are commonly used in the art.

The recombinant vector may include the polynucleotide sequence and a promoter operatively linked to the polynucleotide sequence.

As used herein, the term "operatively linked" refers to a functional linkage between a nucleotide expression control sequence (e.g., a promoter sequence) and another nucleotide sequence, whereby the control sequence controls the transcription and/or translation of the other nucleotide sequence.

Recombinant vectors that may be used in the present disclosure may be constructed by engineering plasmids (e.g., pSC101, ColE1, pBR322, pUC8/9, pHC79, pUC19, pET, etc.), phages (e.g., λgt4λB, λ-Charon, λΔz1 and M13, etc.), or viruses (e.g., SV40, etc.), which are commonly used in the art.

The recombinant vector may include a tag sequence facilitating purification of the conjugate of the cell-penetrating peptide and a skin physiologically active molecule, for example, a continuous histidine codon, a maltose-binding protein codon, a Myc codon, etc. and may further include a fusion partner for increasing the solubility of the conjugate. In addition, the recombinant vector may include a sequence that is specifically cleaved by an enzyme in order to remove an unnecessary portion when the conjugate is expressed, an expression control sequence, and a marker or reporter gene sequence for identifying intracellular delivery.

Yet another aspect of the present disclosure provides a host cell including the recombinant vector, that is, a cell transformed with the recombinant vector.

A host cell that is capable of stably and consecutively cloning or expressing the recombinant vector may be any host cell known in the art. Prokaryotic cells include, for example, *E. coli* JM109, *E. coli* BL21, *E. coli* RR1, *E. coli* LE392, *E. coli* B, *E. coli* X 1776, and *E. coli* W3110. When the recombinant vector is transformed into eukaryotic cells, *Saccharomyces cerevisiae*, insect cells, plant cells and animal cells, for example, SP2/0, CHO (Chinese hamster ovary) K1, CHO DG44, PER.C6, W138, BHK, COS-7, 293, HepG2, Huh7, 3T3, RIN and MDCK cell lines, may be used as host cells.

The polynucleotide or the recombinant vector containing the same may be transferred into the host cell using a transfer method well-known in the art. As the transfer method, for example, when the host cell is a prokaryotic cell, a $CaCl_2$ method or an electroporation method may be used, and when the host cell is a eukaryotic cell, a microinjection method, a calcium phosphate precipitation method, an electroporation method, a liposome-mediated transfection method or a gene bombardment method may be used, but the transfer method is not limited thereto.

A method of selecting the transformed host cell may be easily carried out using a phenotype expressed by a selection marker according to a method known in the art. For example, when the selection marker is a specific antibiotic resistance gene, the transformant may be easily selected by culturing the transformant in a medium containing the antibiotic.

Still yet another aspect of the present disclosure provides a method for producing a conjugate, the method including steps of: culturing the host cell in a culture medium; and recovering the conjugate from the culture medium.

In one embodiment of the present disclosure, the culture of the cell may be large-scale cell culture, and the culture of the cell may be performed using a cell culture method which is commonly used. For example, the cell culture method may be any one or more selected from the group consisting of batch culture, repeated batch culture, fed-batch culture, repeated fed-batch culture, continuous culture, and perfusion culture, but is not limited thereto.

In one embodiment of the present disclosure, the step of recovering the conjugate from the culture medium may be performed using various separation and purification methods known in the art. Generally, the cell lysate may be centrifuged to remove cell debris, culture impurities, etc., and then precipitation, for example, salting out (ammonium sulfate precipitation and sodium phosphate precipitation), solvent precipitation (protein fraction precipitation using acetone, ethanol, isopropyl alcohol, etc.) or the like, may be performed, and dialysis, electrophoresis, and various column chromatographies may be performed.

A further aspect of the present disclosure provides a cosmetic composition for skin condition improvement including, as an active ingredient, either the conjugate, or a cell-penetrating peptide consisting of the amino acid sequence of SEQ ID NO: 1 or SEQ ID NO: 2, and a polypeptide consisting of the amino acid sequence of SEQ ID NO: 5.

In one embodiment of the present disclosure, the skin condition improvement may include wrinkle reduction, skin regeneration, skin elasticity improvement, and skin anti-aging.

Epidermal growth factor (SEQ ID NO: 5) and a cell-penetrating peptide, for example, a cell-penetrating peptide consisting of the amino acid sequence of SEQ ID NO: (ACP) or SEQ ID NO: 2 (ACP2) have excellent skin-penetrating activity even when they are used in the form of a mixture rather than a conjugate, and thus these may be used as a cosmetic composition in the form of a mixture rather than a conjugate.

In one embodiment of the present disclosure, the cosmetic composition may be prepared as a formulation selected from the group consisting of emulsion, cream, essence, skin lotion, liposomes, microcapsules, composite particles, shampoo, and rinse. In addition, the conjugate, or the cell-penetrating peptide consisting of the amino acid sequence of SEQ ID NO: 1 or SEQ ID NO: 2 and the polypeptide consisting of the amino acid sequence of SEQ ID NO: 5 can penetrate the stratum corneum of the skin, and thus the cosmetic composition is most preferably transdermal.

The cosmetic composition may further include an antimicrobial agent, a moisturizing or hydration agent, a preservative, an emulsifier, a natural oil or synthetic oil, a solvent, a surfactant, a detergent, a gelling agent, an emollient, an antioxidant, fragrance, a filler, a thickener, wax, an odor absorber, a dyestuff, a colorant, powder, a viscosity-controlling agent and water, in addition to the conjugate, or the cell-penetrating peptide consisting of the amino acid sequence of SEQ ID NO: 1 or SEQ ID NO: 2 and the polypeptide consisting of the amino acid sequence of SEQ ID NO: 5. Optionally, the cosmetic composition may include a botanical extract, a conditioning agent, a darkening or lightening agent, a glitter, a humectant, minerals, polyphenol, silicone or its derivative, a sunblock, vitamins, and phytomedicinal products.

Another further aspect of the present disclosure provides a pharmaceutical composition for wrinkle reduction, muscle stiffness relief or skin wound healing, the pharmaceutical composition including, as an active ingredient, either the conjugate, or a cell-penetrating peptide consisting of the amino acid sequence of SEQ ID NO: 1 or SEQ ID NO: 2, and a polypeptide consisting of the amino acid sequence of SEQ ID NO: 5.

As used herein, the term "skin wound" refers to a condition in which skin tissue is damaged by a physical cause or the like, and includes defects of epidermal, dermal or subcutaneous tissue. Treatment of skin wounds means restoring the skin to its pre-injury state, and includes reducing and alleviating skin wounds and ameliorating the symptoms of skin wounds.

Epidermal growth factor (SEQ ID NO: 5) and a cell-penetrating peptide, for example, a cell-penetrating peptide consisting of the amino acid sequence of SEQ ID NO: (ACP) or SEQ ID NO: 2 (ACP2), have excellent skin-penetrating activity even when they are used in the form of a mixture rather than a conjugate, and thus these may be used as a pharmaceutical composition for wrinkle reduction, muscle stiffness relief or skin wound healing in the form of a mixture rather than a conjugate.

The pharmaceutical composition of the present disclosure may include a pharmaceutically acceptable carrier, if necessary, in addition to the conjugate; or the cell-penetrating peptide consisting of the amino acid sequence of SEQ ID NO: 1 or SEQ ID NO: 2, and the polypeptide consisting of the amino acid sequence of SEQ ID NO: 5.

These pharmaceutically acceptable carriers are those that are commonly used in the manufacture of pharmaceuticals, and examples thereof include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, and the like. In addition, the pharmaceutical composition of the present disclosure may further include additives such as a lubricant, a wetting agent, a sweetener, a flavoring agent, an emulsifying agent, a suspending agent, a preservative, etc.

The carrier may be included in an amount of about 1 wt % to about 99.99 wt %, preferably about 90 wt % to about 99.99 wt %, based on the total weight of the pharmaceutical composition of the present disclosure, and the additives may be included in an amount of about 0.1 wt % to about 20 wt %, based on the total weight of the pharmaceutical composition of the present disclosure.

Meanwhile, the pharmaceutical composition of the present disclosure may be administered orally or parenterally, but may be administered directly to the skin by a topical administration method.

The pharmaceutical composition of the present disclosure may be formulated with a pharmaceutically acceptable carrier and/or excipient and prepared in a unit dose form or contained in a multi-dose container. In this regard, the formulation may be in the form of a solution, a suspension or an emulsion, or may include elixir, extract, powder, granule, tablet, plaster, liniment, lotions, ointment, etc.

The daily dose of the pharmaceutical composition of the present disclosure may generally be in the range of 0.001 to 150 mg/kg of body weight, and may be administered once or several times. However, the dose of the pharmaceutical composition of the present disclosure is determined in view of various related factors such as the route of administration, the patient's age, sex and body weight, and the severity of the patient, and thus the dose should not be understood to limit the scope of the present disclosure in any way.

Still another further aspect of the present disclosure provides a method for wrinkle reduction, muscle stiffness relief or skin wound healing, the method comprising a step of administering the composition to a subject.

The subject refers to an animal, and may typically be a mammal capable of exhibiting a beneficial effect by treatment with the conjugate or polypeptide of the present disclosure. Preferred examples of such subjects may include primates such as humans. In addition, such subjects may include all subjects who have symptoms of wrinkles, muscle stiffness or skin wounds or are at risk of having such symptoms.

Yet another further aspect of the present disclosure provides the use of either the conjugate, or a cell-penetrating peptide consisting of the amino acid sequence of SEQ ID NO: 1 or SEQ ID NO: 2, and a polypeptide consisting of the amino acid sequence of SEQ ID NO: 5, in the manufacture of a medicament for wrinkle reduction, muscle stiffness relief or skin wound healing.

MODE FOR INVENTION

Hereinafter, the present disclosure will be described in more detail with reference to one or more examples. However, these examples are to illustrate the present disclosure, and the scope of the present disclosure is not limited to these examples.

Example 1: Construction of Cell Penetrating Peptide-Botulinum Toxin Conjugate

As a cell-penetrating peptide, each of ACP (advanced cell penetrating peptide; SEQ ID NO: 1), ACP2 (SEQ ID NO: 2) and ACP1 (SEQ ID NO: 3) was used.

1-1. Construction of Recombinant Vector for Expressing ACP-BTLC

In order to add restriction enzyme recognition sequences so that the restriction enzyme NcoI (New England Biolabs, NEB; USA) could act on the N-terminus of the ACP gene sequence (SEQ ID NO: 13) and HindIII could act on the C-terminus thereof, polymerase chain reaction (hereinafter, referred to as PCR) was performed using primers including the restriction enzyme recognition sequences. Tables 1 and 2 below show the primer sequences and PCR conditions used in the PCR.

TABLE 1

| Primers | SEQ ID NOs. | Sequences |
|---|---|---|
| Forward (from ACP-NcoI) | 25 | CCATGGGCCAGCGGGGAAACCAGC |

TABLE 1-continued

| Primers | SEQ ID NOs. | Sequences |
|---|---|---|
| Reverse (from ACP-HindIII) | 26 | AAGCTTGTTAAGTTTGCCTGTCTCTCTGTGC |

TABLE 2

| PCR reactants | | PCR cycles | |
|---|---|---|---|
| dH$_2$O | 37.5 µl | 95° C. | 2 min |
| dNTP (10×) | 4 µl | 95° C. | 1 min |
| F primer (10 µM) | 1 µl | 55° C. | 30 sec |
| R primer (10 µM) | 1 µl | 74° C. | 4 min |
| ACP peptide gene | 1 µl | 74° C. | 5 min |
| DNA Taq polymerase buffer | 0.5 µl 5 µl | 4° C. | Infinity |
| Total | 50 µl | | |

30 cycles

Thereafter, a pET28a vector (Novagen, USA) was cleaved with NcoI and HindIII restriction enzymes at 37° C. for 2 hours, and the vector fragment was isolated using a PCR purification kit (Qiagen, USA) according to the manufacturer's protocol. The isolated pET28a vector fragment and the PCR product of 1-1 were ligated together, and then the recombinant vector was isolated using the PCR purification kit. The recombinant vector having the ACP gene inserted therein was named pET28a ACP. The ligation reaction conditions for constructing the pET28a ACP vector are shown in Table 3 below.

TABLE 3

| dH$_2$O | 5.5 µl |
|---|---|
| T4 DNA ligase buffer (10×) | 1 µl |
| ACP DNA (50 ng/µl) | 0.5 µl |
| pET28a vector (50 ng/µl) | 2 µl |
| T4 DNA Ligase (400 units/µl) | 1 µl |
| Total | 10 µl |

Thereafter, in the same manner as described above, restriction enzyme recognition sequences were added so that HindIII could act on the N-terminus of botulinum toxin (hereinafter, referred to as BTLC) gene (SEQ ID NO: 16) and XhoI could act on the C-terminus thereof. Table 4 below shows the primer sequences used for amplification of the BTLC gene.

TABLE 4

| Primers | SEQ ID NOs. | Sequences |
|---|---|---|
| Forward (from BTLC-HindIII) | 27 | AAGCTTCCGTTCGTTAACAAACAGTTCAACTACAAAGA |
| Reverse (from BTLC-XhoI) | 28 | CTCGAGTCATTTGTTGTAGCCTTTGTCCAGGGATTT |

A pET28a ACP vector was cleaved with HindIII and XhoI restriction enzymes, and then the vector fragment was isolated using a PCR purification kit. The isolated pET28a ACP vector fragment and the BTLC gene were ligated together, and then the recombinant vector was isolated using the PCR purification kit. The recombinant vector having the ACP-BTLC gene inserted therein was named pET28a ACP-BTLC. The reaction of ligation of the pET28a ACP vector fragment and the BTLC gene was performed under the same conditions as shown in Table 3 above, except that the pET28a ACP vector and the BTLC gene were used. His tag for confirming expression of the recombinant protein was linked to the C-terminus of the ACP-BTLC protein.

E. coli DH5a was transformed with the pET28a ACP-BTLC vector and shake-cultured in LB liquid medium at 37° C. until the OD value reached 0.5 to 0.6. After completion of culture, the cell culture was centrifuged, the E. coli pellet was collected, and the pET28a ACP-BTLC vector was isolated therefrom using a plasmid extraction miniprep kit (Intron, Korea). The concentration of the isolated pET28a ACP-BTLC vector was measured by a UV spectrophotometric method.

1-2. Construction of Recombinant Vectors for Expressing ACP2-BTLC, ACP1-BTLC and BTLC-ACP Recombinant vectors for expressing a conjugate of ACP2 or ACP1 and BTLC, and a conjugate (BTLC-ACP) in which ACP is conjugated to the C-terminus of BTLC, were constructed.

In order to add restriction enzyme recognition sequences so that NdeI could act on the N-terminus of a polynucleotide (SEQ ID NO: 14 or 15) encoding ACP2 or ACP1, HindIII could act on the C-terminus thereof, HindIII could act on the N-terminus of the ACP1 gene and XhoI could act on the C-terminus of the ACP1 gene, PCR was performed under the conditions shown in Table 2. The primer sequences used in the PCR are shown in Table 5 below.

TABLE 5

| Primers | SEQ ID NOs. | Sequences |
|---|---|---|
| Forward (from ACP2-NdeI) | 29 | CATATGAAGTGCTTCAATTGCGGAAAGGAG |
| Reverse (from ACP2-HindIII) | 30 | AAGCTTGCCTTTCTTTCTGGGGGC |
| Reverse (from ACP1-HindIII) | 31 | AAGCTTCTCTGTGCAGTCCTTCATCTGG |
| Forward (from ACP-HindIII) | 32 | AAGCTTCAGCGGGGAAAC |
| Reverse (from ACP-XhoI) | 33 | CTCGAGTAAGTTTGCCTG |

Thereafter, a pET28a vector was cleaved with NdeI and HindIII or HindIII and XhoI, and the vector fragment was isolated. Under the conditions shown in Table 3, the isolated pET28a vector fragment and each of the ACP2, ACP1 and ACP genes, to which the restriction enzyme recognition sequences were added, were ligated together. Then, the recombinant vectors were isolated using a PCR purification kit. The recombinant vectors having ACP2, ACP1 and ACP genes inserted therein were named pET28a ACP2, pET28a ACP1, and pET28a ACP (C-terminus), respectively.

Next, PCR was performed under the same conditions shown in Table 2, in order to add restriction enzyme recognition sequences so that HindIII could act on the N-terminus of the BTLC gene and XhoI could act on the C-terminus thereof, or NcoI could act on the N-terminus thereof and HindIII could act on the C-terminus thereof. In the PCR, the primers shown in Table 4 above and Table 6 below were used.

TABLE 6

| Primers | SEQ ID NOs. | Sequences |
|---|---|---|
| Forward (from BTLC-NcoI) | 34 | CCATGGGCCCGTTCGTTAACAAACAGTTCAACTACAAAGA |
| Reverse (from BTLC-HindIII) | 35 | AAGCTTTTTGTTGTAGCCTTTGTCCAGGGATTT |

The pET28a ACP2 and pET28a ACP1 vectors were cleaved with HindIII and XhoI, and the pET28a ACP1 (C-terminus) vector was cleaved with NcoI and HindIII. The vector fragments were isolated. Each of the isolated pET28a ACP2, pET28a ACP1 and pET28a ACP (C-terminus) vector fragments and the BTLC gene were ligated together, and the recombinant vectors were isolated using a PCR purification kit. The recombinant vectors having ACP2-BTLC, ACP1-BTLC and BTLC-ACP genes inserted therein were named pET28a ACP2-BTLC, pET28a ACP1-BTLC, and pET28a BTLC-ACP, respectively. The reaction for ligation of each of the pET28a ACP2, pET28a ACP1 and pET28a ACP (C-terminus) vector fragments and the BTLC gene was performed in the same conditions as shown in Table 3 above, except the vectors and the BTLC gene. His tag for confirming expression of the recombinant protein was linked to the N-terminus of each protein to be expressed.

1-3. Recombinant Vector for Expressing BTLC

PCR was performed under the same conditions as shown in Table 2 above, in order to add restriction enzyme recognition sequences so that NcoI could act on the N-terminus of the BTLC gene and XhoI could act on the C-terminus thereof. In the PCR, the primer of SEQ ID NO: 34 shown in Table 6 and the primer shown in Table 7 below were used.

TABLE 7

| Primer | SEQ ID NO | Sequence |
|---|---|---|
| Reverse (from BTLC-XhoI) | 36 | CTCGAGTTTGTTGTAGCCTTTGTCCAGGGATTT |

A pET28a vector was cleaved with NcoI and XhoI restriction enzymes, and then the vector fragment was isolated. Under the conditions shown in Table 3, the pET28a vector fragment and the BTLC gene were ligated together. The recombinant vector was isolated using a PCR purification kit, and the recombinant vector having the BTLC gene inserted therein was named pET28a BTLC.

1-4. Analysis of Expression of Cell Penetrating Peptide-Botulinum Toxin Conjugate BL21(DE3) (Thermo Fisher, USA) was transformed with each of the pET28a ACP-BTLC, pET28a ACP2-BTLC, pET28a ACP1-BTLC, pET28a BTLC-ACP and pET28a BTLC vectors, and then plated on an LB (Luria-Bertani) plate, followed by culture at 37° C. for 12 hours. After 12 hours, the formed colony was inoculated into LB liquid medium and further pre-cultured at 37° C. After about 12 hours, 250 μl of the cell pre-culture that reached an OD value of 0.5 to 0.6 was inoculated into 250 ml of LB liquid medium, and cultured at 37° C. for 3 hours to 4 hours until the OD value reached 0.6 to 0.8. When the OD value of the cell culture reached 0.6 to 0.8, 0.25 mM of IPTG (isopropyl β-D-thiogalactoside) was added to the cell culture which was then cultured at 16° C. for 18 hours. After 18 hours, the cell culture was centrifuged, and the BL21 pellet was collected. The collected pellet was suspended in a lysis buffer (20 mM Tris, 300 mM NaCl, 5 mM imidazole and pH 8.0), and then the *E. coli* cells were lysed by sonication at an amplitude of 35%.

The *E. coli* cell lysate was centrifuged, and the supernatant was collected. The supernatant was filled into a tube through a 0.45 μm filter. The supernatant filled in the tube was loaded into a column packed with Ni-NTA (nitrilotriacetic acid) resin so that the protein was bound to the resin. To remove foreign proteins unbound to the resin, the resin was washed by adding a washing buffer (20 mM Tris, 300 mM NaCl, 30 mM imidazole and pH 8.0) thereto. Thereafter, the protein was eluted with a gradient mobile phase using a buffer (20 mM Tris, 300 mM NaCl, 400 mM imidazole and pH 8.0) containing imidazole. To additionally remove foreign proteins and to remove imidazole, the collected protein was subjected to size exclusion chromatography. The chromatography was performed using a washing buffer (25 mM HEPES, 100 mM NaCl, 2 mM DTT and pH 7.4). The concentration of the purified protein was measured by Bradford assay.

1-5. Construction of Recombinant Vector for Expression in Animal Cells

Each of the pET28a BTLC, pET28a ACP-BTLC, pET28a ACP1-BTLC and pET28a ACP2-BTLC vectors constructed in 1-2 above was cleaved with NcoI and XhoI, and a pTriEx vector was cleaved with the same restriction enzymes and isolated. Under the conditions shown in Table 3 above, the two fragments were ligated together. The resulting vectors were named pTriEx BTLC, pTriEx ACP-BTLC, pTriEx ACP1-BTLC, and pTriEx ACP2-BTLC, respectively.

Example 2: Characterization of Conjugate of Cell-Penetrating Peptide and Botulinum Toxin 2-1. Analysis of Cell Penetration HeLa cells were cultured in a DMEM medium supplemented with 10% FBS (fetal bovine serum) and 100 U/ml penicillin/streptomycin, U87-MG and PC-12 cells were cultured in an RPMI-1640 medium (Hyclone, USA) supplemented with 10% FBS and 100 U/ml penicillin/streptomycin. All the cells were cultured in a humidified incubator at 37° C. under 5% $CO_2$.

Each type of the cultured cells was seeded into a 12-well plate containing glass at a density of $1 \times 10^5$ cells/well and cultured for 24 hours. Thereafter, the cells were treated with each of the BTLC, ACP-BTLC, ACP1-BTLC and ACP2-BTLC purified in Example 1-4 above for 3 hours, and then the cells were washed three times with PBS. The washed cells were fixed with 3.7% formaldehyde for 20 minutes, and treated with PBS containing 0.2% Triton X-100 to increase cell membrane penetration. Next, the cells were treated and blocked with 3% BSA for 1 hour, incubated with anti-His antibody (Abcam, ab9108) at room temperature for 2 hours, and then washed three times with PBS. After washing, the cells were treated and incubated with Alexa 488 and Alexa 568 secondary antibodies (Santa Cruz Biotechnology) at room temperature for 1 hour. Next, the cells were washed twice with PBS, and then stained with DAPI (4',6-diamidino-2-phenylindole) for 10 minutes. The glass, to which the cells were attached, was detached, placed on slide glass, and observed by confocal laser scanning microscopy (LSM 700, Zeiss, Germany).

As a result, as shown in FIGS. 1A to 1C, it could be confirmed that BTLC alone hardly penetrated the HeLa, U87-MG and PC-12 cells, but ACP-BTLC had excellent cell-penetrating ability.

Figure 2:
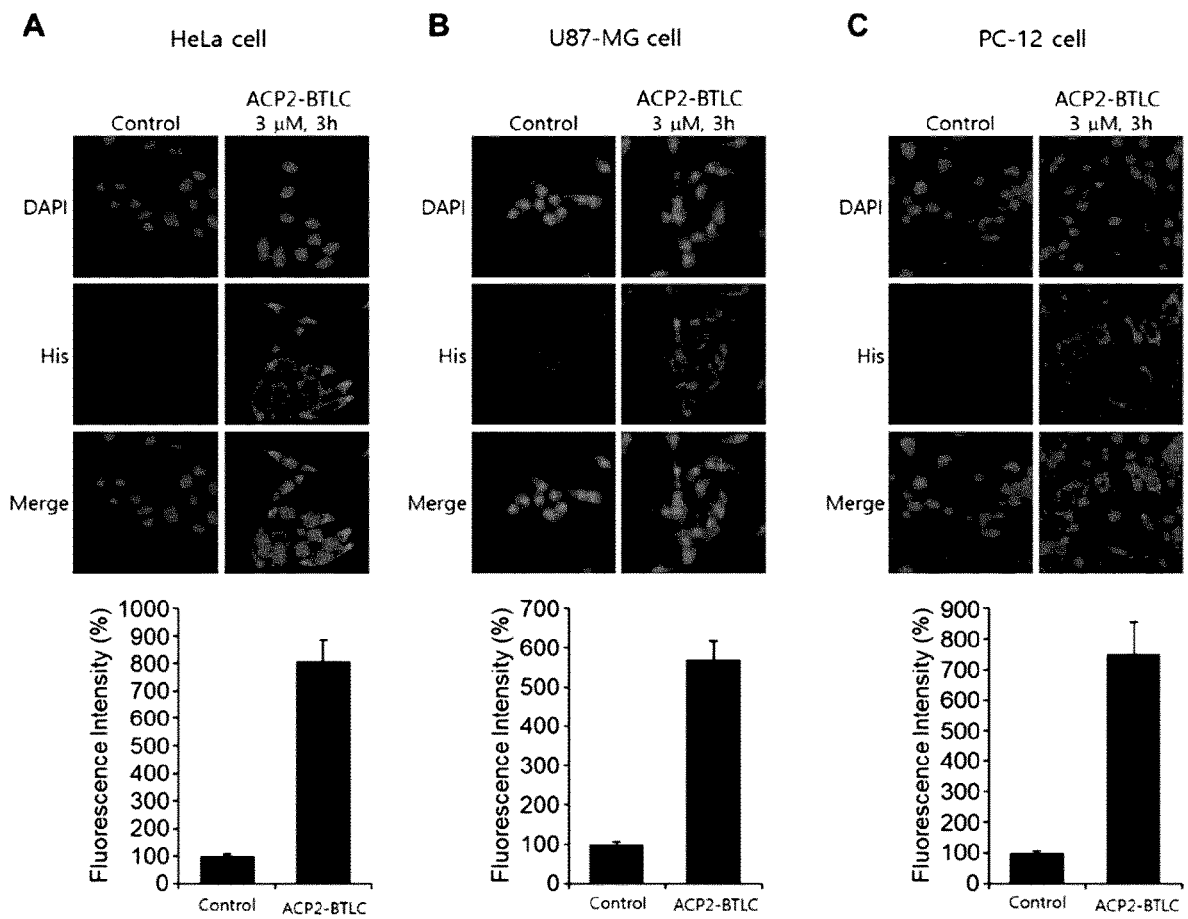
FIG. 2 shows the results of analyzing the cell membrane-penetrating activity of ACP2-BTLC in HeLa cells (A), U87-MG cells (B) and PC-12 cells (C).
Figure 3:
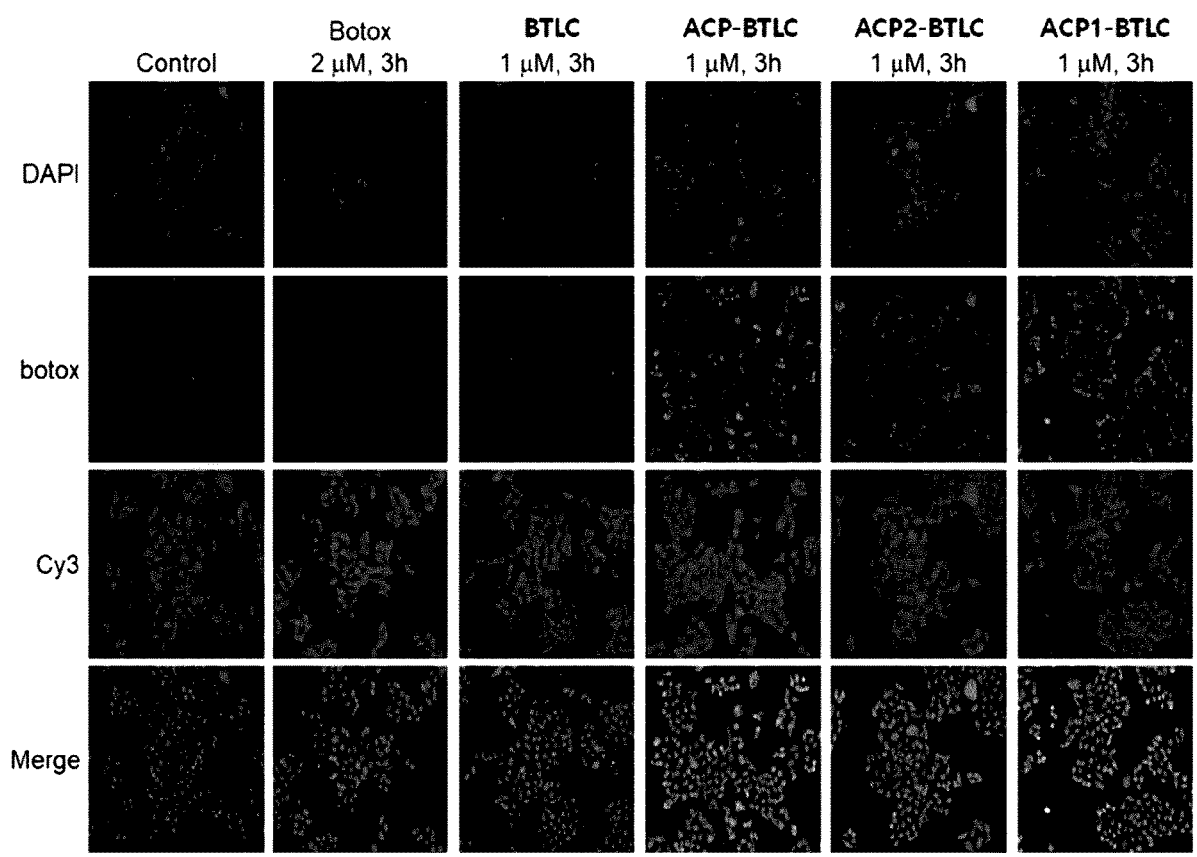
FIG. 3 shows the results of analyzing the cell membrane-penetrating abilities of conjugates of different cell-penetrating peptides and botulinum toxin in HeLa cells.

In addition, as shown in FIGS. 2A to 2C, it could be seen that ACP2-BTLC also had excellent cell-penetrating ability compared to the control for all the cells. From FIG. 3, it could be confirmed that ACP-BTLC, ACP1-BTLC and ACP2-BTLC had better cell-penetrating ability than BTLC. In FIG. 3, botox used as a positive control is Onabotulinum toxin A (Allergen, USA), a commercially available product.

2-2. Analysis of Penetration into Mouse Skin Tissue

Gauze was placed on a 6-well plate, and 3 ml of RPMI medium was added to each well of the plate. Skin tissue having a size of 0.5 cm×0.5 cm, isolated from nude mice (Orient Bio Co., Ltd., Korea) was gently placed on the gauze, and Whatman paper was placed on the mouse skin tissue. Thereafter, the Whatman paper was treated and reacted with various concentrations of BTLC or ACP-BTLC for hours. The mouse skin tissue was fixed with 4% paraformaldehyde for 1 hour, and placed in 30% sucrose until the skin tissue was settled. The skin tissue was frozen with OCT compound (Leica, Germany) and sectioned with a cryostat microtome, thus preparing skin tissue section slides. The slides were stained with anti-His antibody and anti-BTLC antibody, stained with DAPI for 10 minutes, and then observed by confocal laser scanning microscopy.

Figure 4:
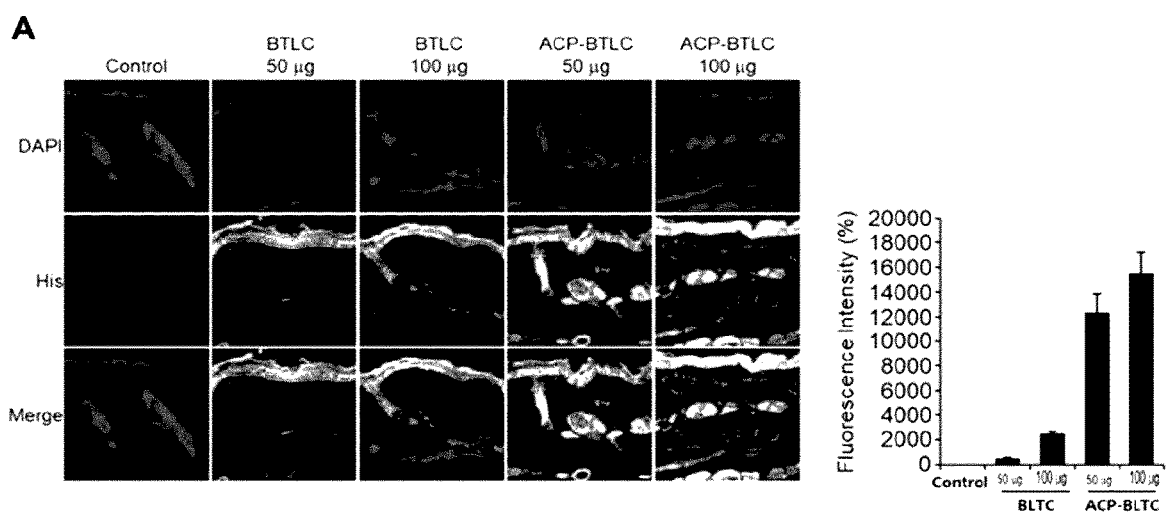
FIG. 4 shows the results of analyzing the mouse skin tissue-penetrating effects of BTLC and ACP-BTLC in a concentration-dependent manner. Specifically.
Figure 4:
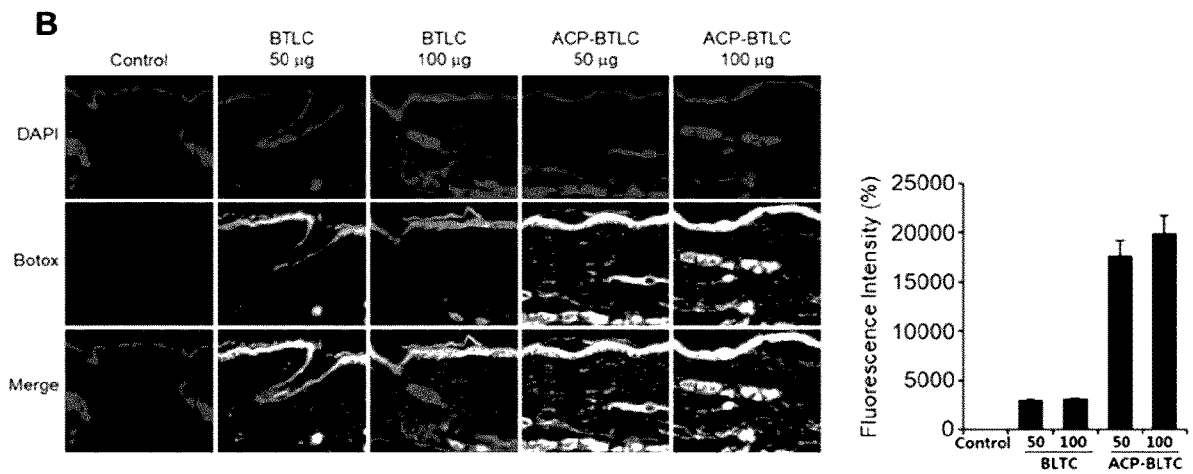

As a result, as shown in FIGS. 4A and 4B, it could be seen that, when the skin tissue was treated with BTLC, a fluorescence signal was weakly observed only on the surface of the skin tissue, suggesting that the BTLC hardly penetrated the skin tissue. On the other hand, it could be confirmed that, when the skin tissue were treated with ACP1-BTLC, a strong fluorescence signal appeared even in the dermal layer of the skin tissue, suggesting that the ACP1-BTLC penetrated deep into the skin tissue.

2-3. Analysis of Whether SNAP25 Protein is Cleaved

Synaptosomal-associated protein 25 (SNAP25) is one of the components of the SNARE complex, and the SNARE complex is involved in acetylcholine signaling and allows muscles to move. It is known that BTLC impairs the movement of muscles by cleaving SNAP25 after entering the nerve terminal. Thus, whether the cell penetrating peptide-botulinum toxin conjugate cleaves SNAP25 was analyzed. [00141]1 μg of SNAP25 (Novus Biologicals, USA) and various concentrations of each of BTLC, ACP-BTLC, ACP1-BTLC and ACP2-BTLC were placed in a 1.5-ml microtube, and a reaction buffer (50 mM HEPES (pH 7.4), 5 mM DTT and 250 μM $ZACPl_2$) was added thereto so that the final volume of each sample was 30 μl. Thereafter, each sample was reacted at 37° C. for 24 hours, and the reaction was terminated by addition of an SDS sample buffer (50 mM Tris-HCl (pH 6.8), 2% SDS (sodium dodecylsulfate), 10% glycerol, 1% β-mercaptoethanol, 12.5 mM EDTA and 0.02% bromophenol blue). Whether SNAP25 was cleaved was analyzed by Western blot analysis.

Figure 5:
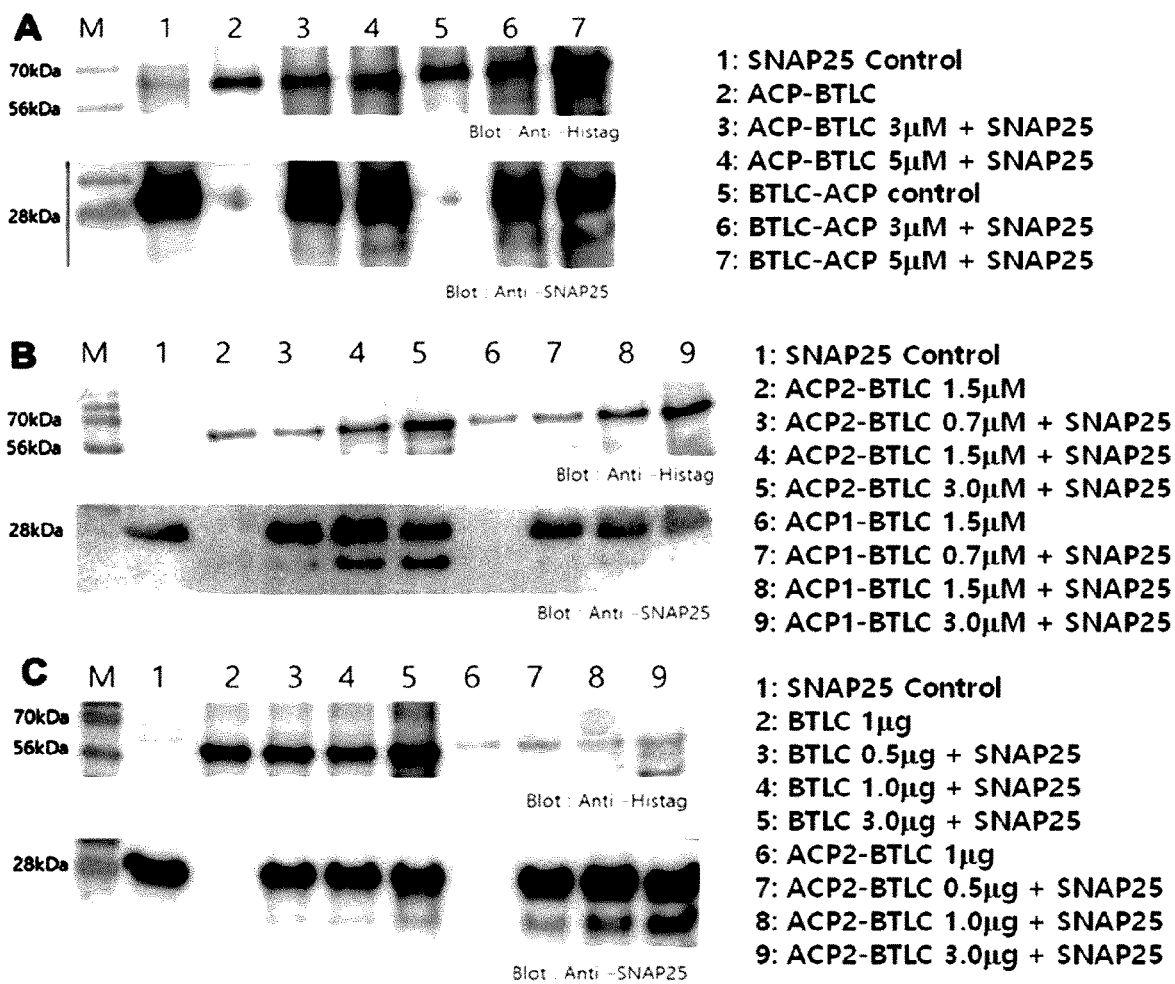
FIG. 5 shows the results of examining whether ACP-BTLC, BTLC-ACP, ACP2-BTLC, ACP1-BTLC and BTLC cleave SNAP25.

As a result, as shown in FIG. 5A, it could be seen that SNAP25 (28 kDa) was cleaved by ACP-BTLC or BTLC-ACP. In addition, as shown in FIGS. 5B and 5C, it could be confirmed that ACP2-BTLC, BTLC and ACP1-BTLC also cleaved SNAP25.

2-4. Analysis of SNAP25 Cleavage by Transfection Assay

Whether the cell penetrating peptide-botulinum toxin conjugate cleaves SNAP25 was analyzed by transfection assay.

Specifically, PC-12 cells, cultured in the same manner as described on 2-1 above, were seeded into a 6-well plate at a density of $3 \times 10^5$ cells/well and cultured for 24 hours. After culture, the cells were transfected with 3 μg of each of pTriEx BTLC, pTriEx ACP-BTLC, pTriEX ACP1-BTLC and pTriEx ACP2-BTLC recombinant vector DNAs using METAFECTENE PRO reagent (Biontex, Germany) according to the manufacturer's protocol. Then, the cells were additionally cultured for 24 hours.

The cultured cells were washed with PBS, and separated from the plates by a scraper. The separated cells were lysed by adding an RIPA buffer (10 mM Tris-Cl (pH 8.0), 1 mM EDTA, 0.5 mM EGTA, 1% Triton X-100, 0.1% sodium deoxycholate, 0.1% SDS, 140 mM NaCl and 1 mM PMSF) thereto, and left to stand on ice for 20 minutes.

Thereafter, cell debris was removed by centrifugation (at 14,000 rpm for 20 min) at 4° C., and only the cell lysate supernatant was collected. The protein concentration of the collected cell lysate was measured by Quick Start™ Bradford 1× Dye Reagent (Bio-Rad, USA), and 20 μg of the protein was separated by 10% SDS-PAGE (sodium dodecyl sulfate-polyacrylamide gel electrophoresis). The separated protein was transferred to a PVDF (polyvinylidene difluoride) membrane, and then the PVDF membrane was blocked with 5% skim milk. The PVDF membrane was incubated with primary antibodies (anti-ACP, anti-His and anti-actin antibodies) at 4° C. for 16 hours, washed, and then incubated with secondary antibodies at room temperature for 1 hour. Thereafter, the protein band was detected using ECL (Pierce™ ECL Western Blotting Substrate (Thermo Scientific™, USA)) according to the manufacturer's protocol. For detection of the protein band, Amersham™ Imager 600 (GE Healthcare Life Science, USA) was used.

Figure 6:
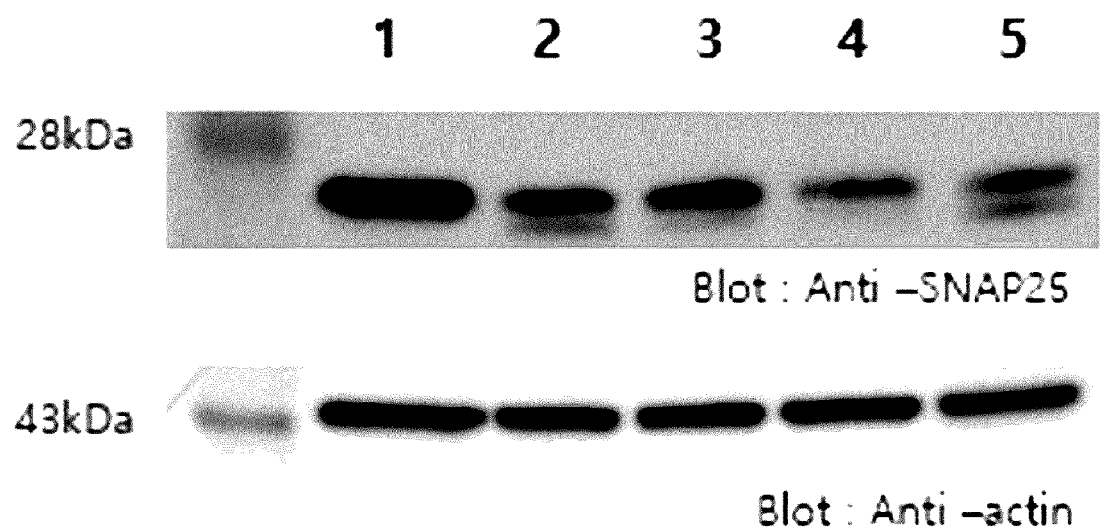
FIG. 6 shows the results of examining whether BTLC, ACP-BTLC, ACP2-BTLC and ACP1-BTLC expression vectors transfected in the same amount cleave SNAP25.

As a result, as shown in FIG. 6, it could be confirmed that SNAP25 (28 kDa) expressed in the PC-12 cells was cleaved by each of BTLC, ACP-BTLC, ACP1-BTLC and ACP2-BTLC.

This experimental result suggests that the cell penetrating peptide-botulinum toxin conjugate retains the activity of botulinum toxin itself.

2-5. Analysis of SNAP25 Cleavage after Cell Penetration

Analysis was made as to whether the cell penetrating peptide-botulinum toxin conjugate retains its SNAP25 cleavage activity even after penetrating cells.

Specifically, PC-12 cells, cultured in the same manner as described in 2-1 above, were seeded into a 6-well plate at a density of $3\times10^5$ cells/well and cultured for 24 hours. Thereafter, the cells were treated with each of BTLC, ACP-BTLC, BTLC-ACP, ACP1-BTLC and ACP2-BTLC (purified in Example 1-4) for 24 hours, and then washed with PBS. According to the method of 2-4 above, protein was collected from the cells, and then the concentration thereof was measured using Quick Start™ Bradford 1× Dye Reagent (Bio-Rad, USA). 20 μg of the protein was separated by 10% SDS-PAGE (sodium dodecyl sulfate-polyacrylamide gel electrophoresis). According to the same method as described in 2-4 above, the separated protein was transferred to a PVDF (polyvinylidene difluoride) membrane, and the protein band was detected using ECL (Pierce™ ECL Western Blotting Substrate (Thermo Scientific™, USA)). For detection of the protein band, Amersham™ Imager 600 (GE Healthcare Life Science, USA) was used.

Figure 7:
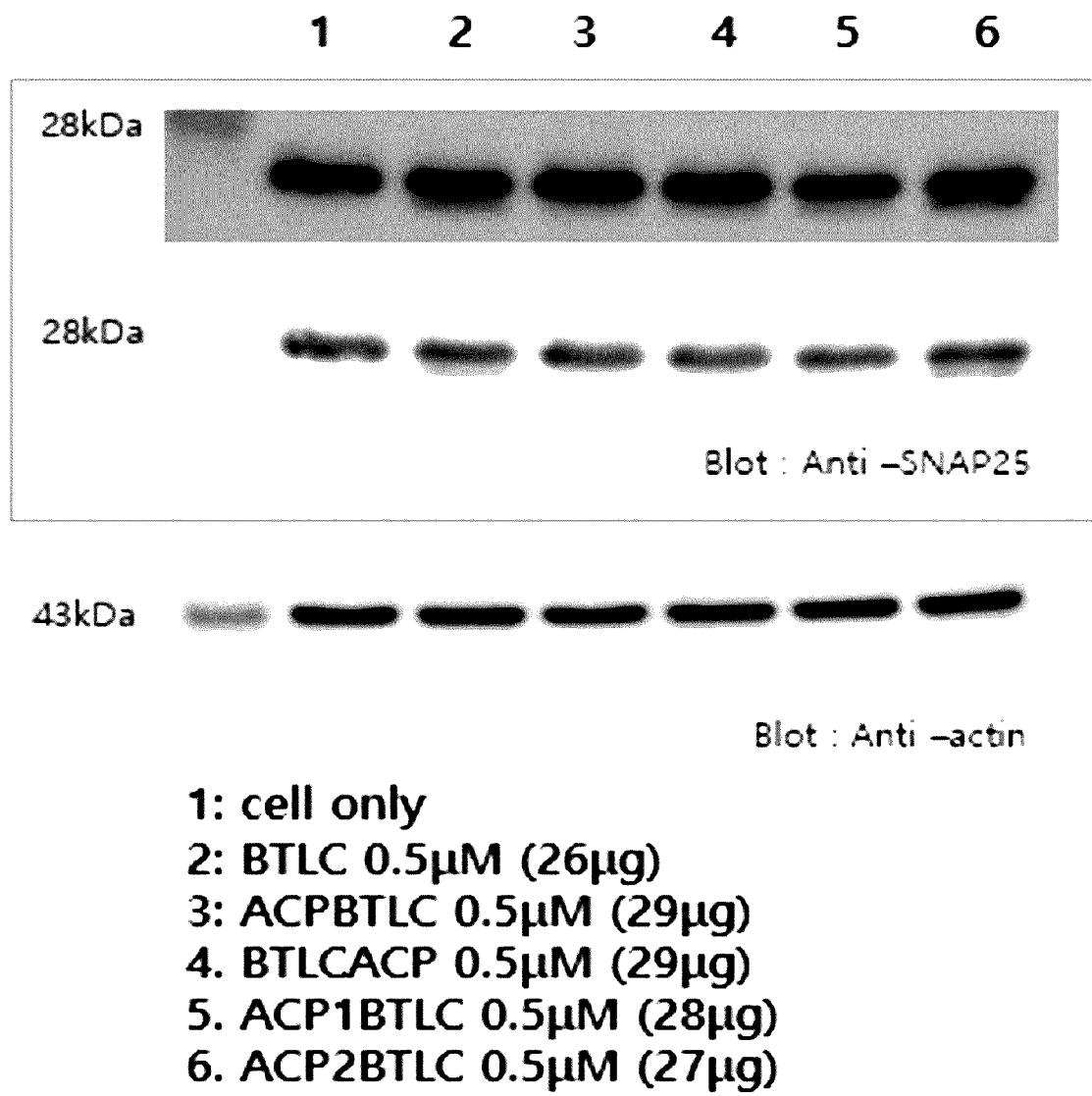
FIG. 7 shows the results of examining whether ACP-BTLC, BTLC-ACP, ACP2-BTLC, ACP1-BTLC and BTLC cleave SNAP25 after cell membrane penetration.

As a result, as shown in FIG. 7, it could be confirmed that each of BTLC, ACP-BTLC, BTLC-ACP, ACP1-BTLC and ACP2-BTLC cleaved SNAP25 (28 kDa) expressed in the PC-12 cells.

This experimental result suggests that the cell penetrating peptide-botulinum toxin conjugate retains the activity of botulinum toxin itself even after penetrating cells.

Example 3: Characterization of Conjugate of Cell-Penetrating Peptide and Epidermal Growth Factor (EGF)

3-1. Synthesis of Epidermal Growth Factor

Epidermal growth factor was synthesized using an FMOC solid-phase method by Chempeptide Limited (Shanghai, China). The synthesized peptide was purified and analyzed by reverse-phase HPLC (HPLC-20AP, Japan) using a C18 analysis RP column (Shiseido Capcell Pak), and identified using a mass spectrometer (SHIMADZU LCMS-2010EV, Japan).

ACP2 used as a cell-penetrating peptide was conjugated to the N-terminus of the epidermal growth factor.

3-2. Analysis of Cell Penetration

According to the same method as described in Example 2-1, HeLa cells were treated with various concentrations of FITC-ACP2 or FITC-ACP2-EGF, and the cells were fixed, and then incubated with anti-Cy3 secondary antibody. The glass, to which the HeLa cells were attached, was detached, placed on slide glass, and observed by confocal laser scanning microscopy.

Figure 8:
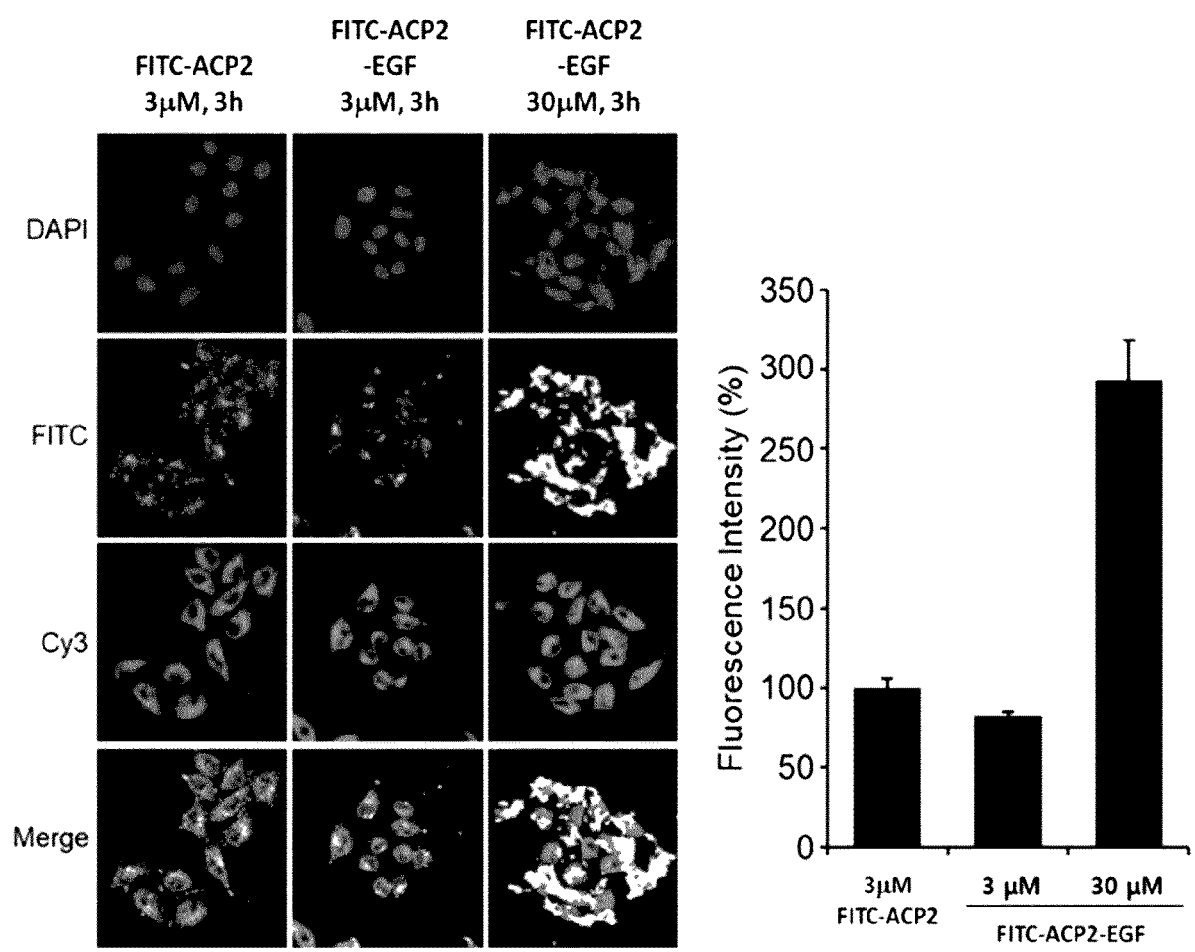
FIG. 8 shows the results of analyzing the cell membrane-penetrating activities of FITC-ACP2 and FITC-ACP2-EGF (epidermal growth factor) in HeLa cells.

As a result, as shown in FIG. 8, it could be confirmed that, in proportion to the treatment concentration, FITC-ACP2-EGF penetrated the cell membrane and entered the cells.

3-3. Analysis of Penetration into Mouse Skin Tissue

According to the same method as described in Example 2-2, mouse skin tissue was treated with EGF (control) or FITC-ACP2-EGF, and then whether EGF or FITC-ACP2-EGF penetrated the skin tissue was observed by confocal laser scanning microscopy.

Figure 9:
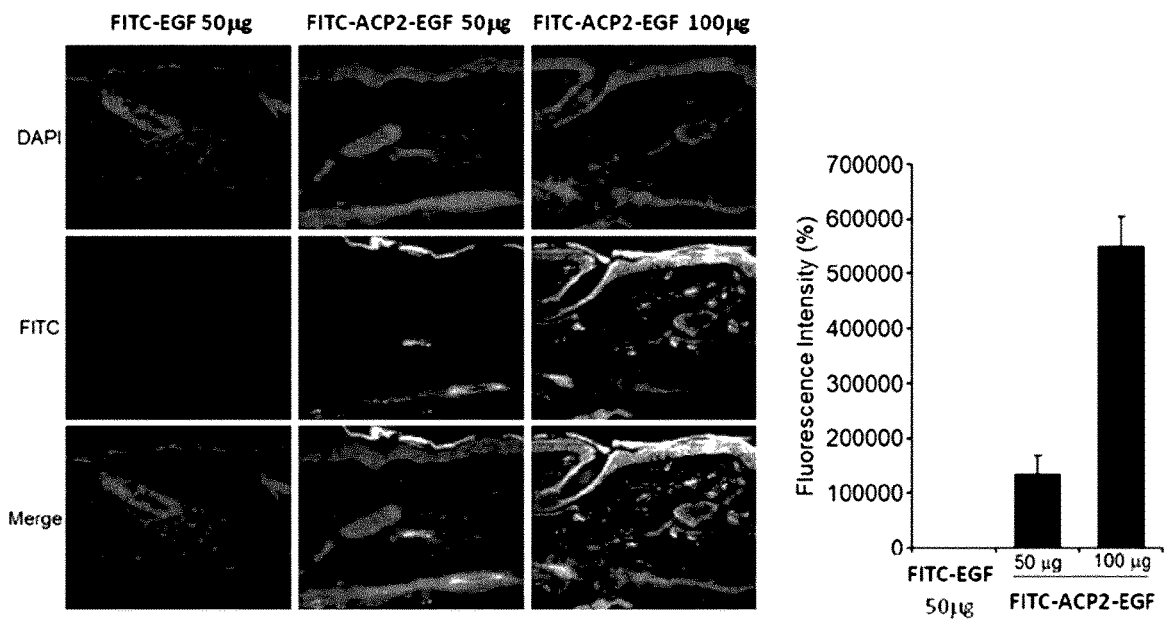
FIG. 9 shows the results of analyzing the mouse skin tissue-penetrating effects of FITC-ACP2-EGF in a concentration-dependent manner.

As a result, as shown in FIG. 9, it could be seen that no fluorescence signal could be observed in the control group, suggesting that the EGF protein alone hardly penetrated the skin tissue. On the other hand, it could be confirmed that, when the skin tissue was treated with FITC-ACP2-EGF, a strong fluorescence signal appeared even in the dermal layer of the skin tissue in a concentration-dependent manner, suggesting that FITC-ACP2-EGF penetrated deep into the skin tissue.

3-3. Analysis of Whether Cell Migration Increases

A431 cells were cultured in an RPMI-1640 medium (Hyclone, USA) supplemented with 10% FBS and 100 U/ml penicillin/streptomycin. The cultured A431 cells were seeded into a 24-well plate containing glass at a density of $1\times10^5$ cells/well, and then cultured for 24 hours. The confluent monolayer cells at the bottom were scraped with a tip, and then the culture medium was replaced with a medium containing 5% FBS and 100 U/ml penicillin/streptomycin. The cells were treated with 1, 5, 10 and 100 nM (11.132, 55.66, 111.32 and 1,113.2 ng/ml) of ACP2-EGF, and a positive control group was treated with 50 ng/ml of recombinant human EGF. The cells were additionally cultured for 18 hours, and then migration of the cells was observed under a microscope.

Figure 10:
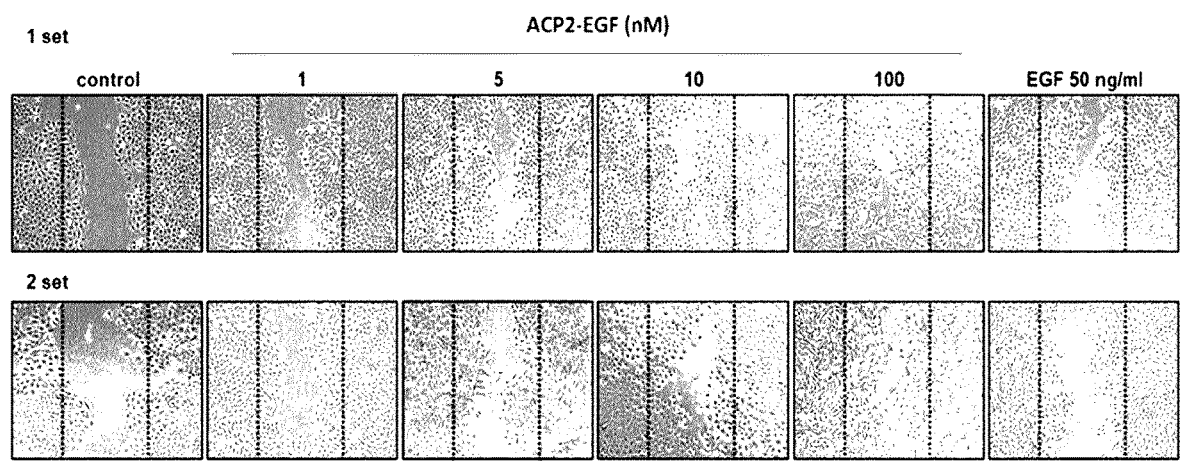
FIG. 10 shows the results of analyzing the effect of ACP2-EGF on increased cell migration in A431 cells.

As a result, as shown in FIG. 10, it could be confirmed that, when the cells were treated with 1 nM (11.132 ng/ml) of ACP2-EGF, the cells showed cell migration similar to the positive control group (50 ng/ml of EGF), and when the cells were treated with 5 nM (55.66 ng/ml) of ACP2-EGF, the cells showed better cell migration than the positive control group.

Example 4: Characterization of Conjugate of Cell-Penetrating Peptide and Hexapeptide 4-1. Synthesis of Hexapeptide According to the same method as described in Example 3-1 above, hexapeptide was synthesized, isolated and purified by Chempeptide Limited (Shanghai, China). ACP2 used as a cell-penetrating peptide was conjugated to the N-terminus of the hexapeptide.

4-2. Analysis of Cell Penetration

According to the same method as described in Example 2-1 above, HeLa cells were treated with various concentrations of FITC-hexapeptide or FITC-ACP2-hexapeptide, and the cells were fixed, and then incubated with anti-Cy3 secondary antibody. The glass, to which the HeLa cells were attached, was detached, placed on slide glass, and observed by confocal laser scanning microscopy.

Figure 11:
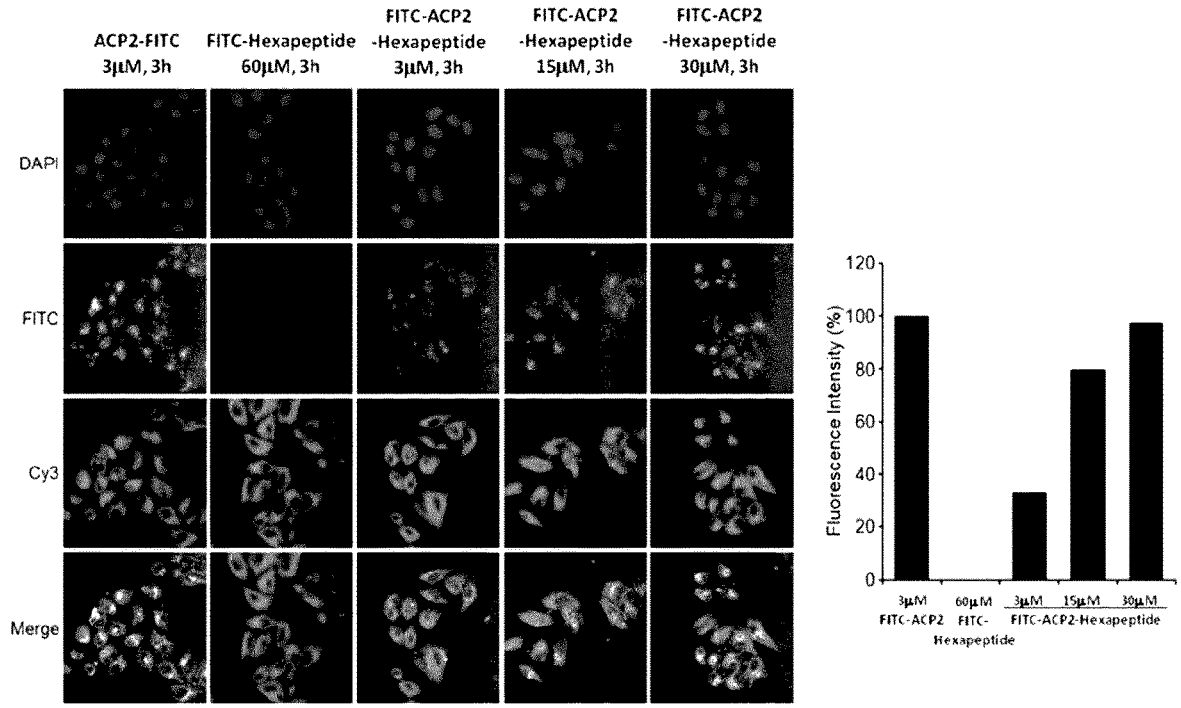
FIG. 11 shows the results of analyzing the cell membrane-penetrating activities of FITC-hexapeptide and FITC-ACP2-hexapeptide in Hela cells in a concentration-dependent manner.

As a result, as shown in FIG. 11, it could be seen that FITC-hexapeptide hardly penetrated the cells, but when the cells were treated with FITC-ACP2-hexapeptide, a strong fluorescence signal appeared, suggesting that the FITC-ACP2-hexapeptide has excellent cell-penetrating ability.

4-3. Analysis of Penetration into Mouse Skin Tissue

According to Example 2-2 above, mouse skin tissue was treated with various concentrations of FITC-hexapeptide or FITC-ACP2-hexapeptide, and then whether FITC-hexapeptide or FITC-ACP2-hexapeptide penetrated the skin tissue was observed by confocal laser scanning microscopy.

Figure 12:
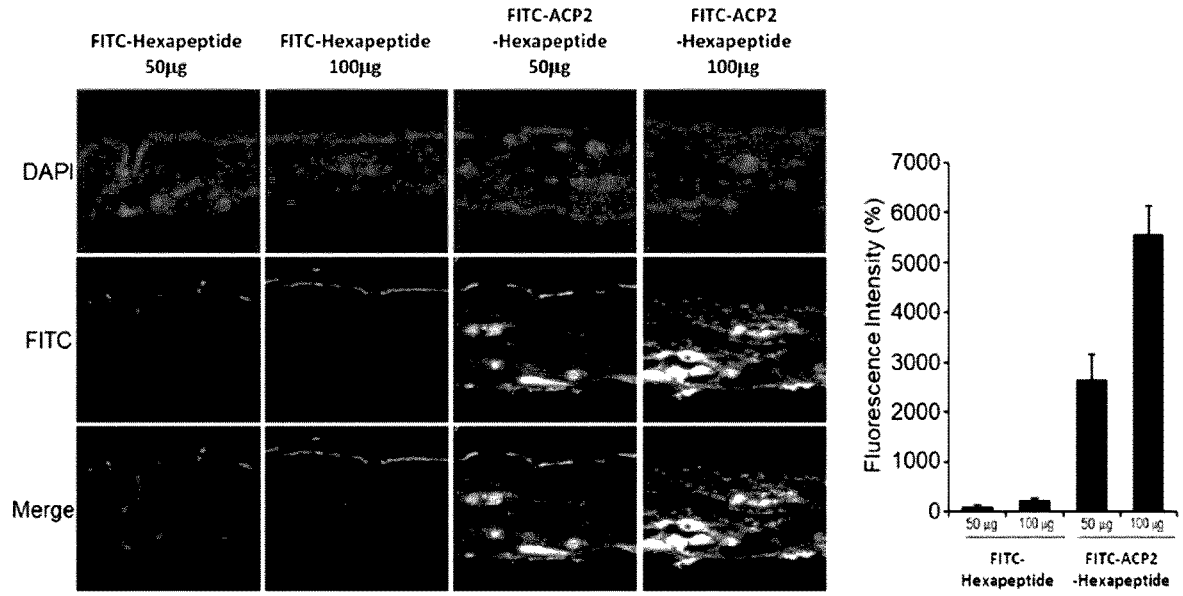
FIG. 12 shows the results of analyzing the mouse skin tissue-penetrating effects of FITC-hexapeptide and FITC-ACP2-hexapeptide in a concentration-dependent manner.

As a result, as shown in FIG. 12, it could be seen that, when the skin tissue was treated with FITC-hexapeptide, a fluorescence signal was weakly observed only on the surface of the skin tissue, suggesting that FITC-hexapeptide hardly penetrated the skin tissue. On the other hand, it could be seen that, when the skin tissue was treated with FITC-ACP2-hexapeptide, a strong fluorescence signal appeared even in the dermal layer of the skin tissue, suggesting that FITC-ACP2-hexapeptide penetrated deep into the skin tissue.

Example 5: Analysis of Cell-Penetrating Activity of Mixture of Cell-Penetrating Peptide and Epidermal Growth Factor 5-1. Analysis of Penetration of Mixture of Cell-Penetrating Peptide and Epidermal Growth Factor into HeLa Cells HeLa cells were cultured in a DMEM medium supplemented with 10% FBS (fetal bovine serum) and 100 U/ml penicillin/streptomycin in a humidified incubator at 37° C. under 5% $CO_2$. The cultured cells were seeded into a 12-well plate containing glass at a density of $1 \times 10^5$ cells/well and cultured for 24 hours. Thereafter, FITC-EGF and ACP were mixed together at room temperature for 30 minutes, and the cells were treated with the mixture for 20 hours, and then washed three times with PBS. The washed cells were fixed with 3.7% paraformaldehyde for 20 minutes, washed twice with PBS, and then stained with DAPI (4',6-diamidino-2-phenylindole) for 10 minutes. The glass, to which the cells were attached, was detached, placed on slide glass, and observed by confocal laser scanning microscopy (LSM 700, Zeiss, Germany).

Figure 13:
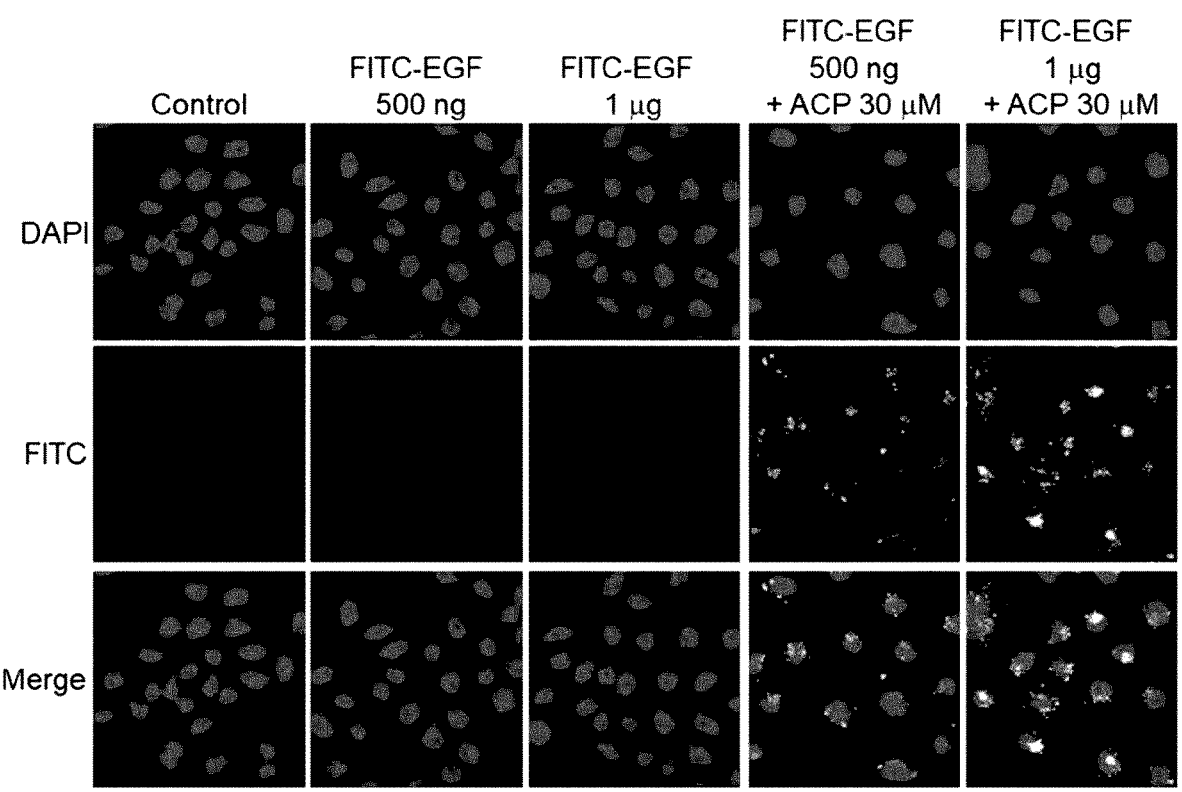
FIG. 13 shows the results of analyzing the cell membrane-penetrating activities of FITC-EGF and FITC-EGF+ACP peptide in HeLa cells.

As a result, it could be confirmed that EGF alone showed no cell penetrating activity, but when the cells were treated with the mixture of EGF and ACP, EGF penetrated the cells (FIG. 13).

5-2. Analysis of Penetration of Mixture of Cell Penetrating Peptide and Epidermal Growth Factor into Mouse Skin Tissue Gauze was placed on a 6-well plate, and 3 ml of RPMI medium was added to each well of the plate. Skin tissue having a size of 0.5 cm×0.5 cm, isolated from nude mice (Orient Bio Co., Ltd., Korea) was gently placed on the gauze, and Whatman paper was placed on the mouse skin tissue. Thereafter, the Whatman paper was treated and reacted with FITC-EGF or various concentrations of a mixture of FITC-EFG and ACP for 12 hours. The mouse skin tissue was fixed with 4% paraformaldehyde for 1 hour, and placed in 30% sucrose until the skin tissue was settled. The skin tissue was frozen with OCT compound (Leica, Germany) and sectioned with a cryostat microtome, thus preparing skin tissue section slides. The slides were stained with DAPI for 10 minutes, and then observed by confocal laser scanning microscopy.

Figure 14:
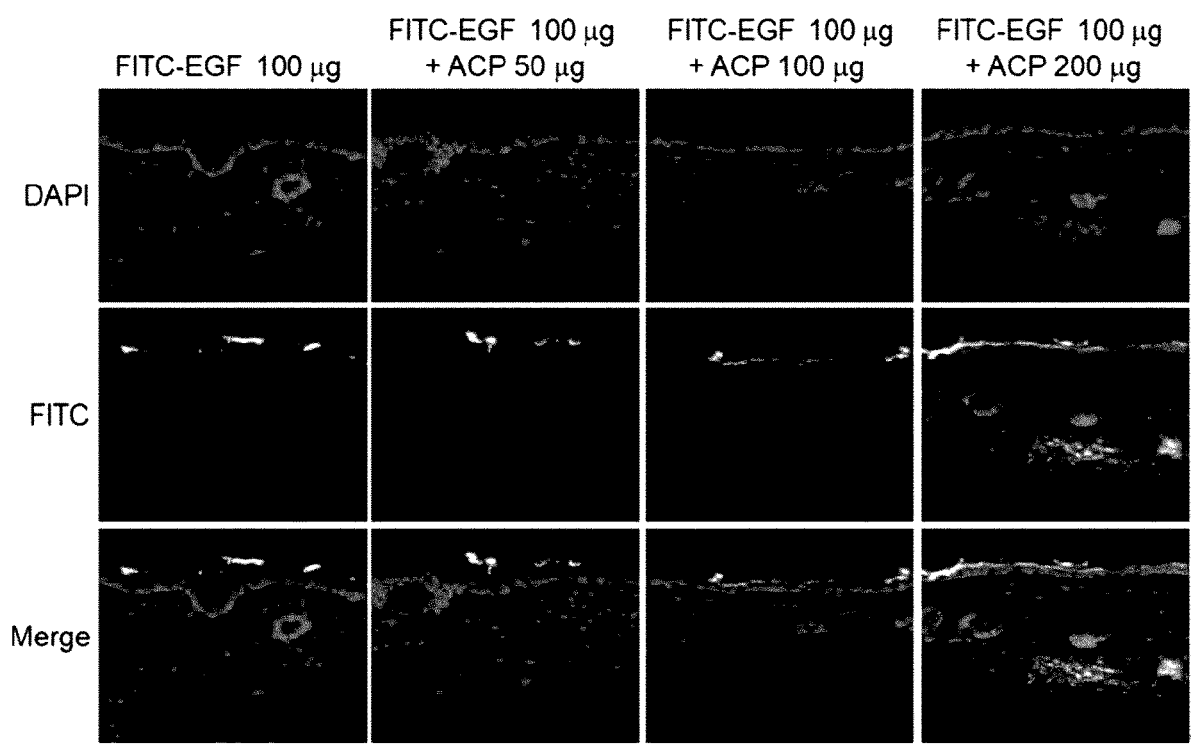
FIG. 14 shows the results of analyzing the mouse skin tissue-penetrating effects of FITC-EGF and FITC-EGF+ACP peptide in a concentration-dependent manner.

As a result, it could be confirmed that EGF alone did not penetrate the mouse skin tissue, but when the skin tissue was treated with the mixture of EGF and ACP, EGF penetrated the mouse skin tissue in a manner dependent on the concentration of ACP (FIG. 14).

5-3. Analysis of Penetration of Mixture of Cell Penetrating Peptide and Epidermal Growth Factor into Minipig Skin Tissue Micropig Franz cell membrane (2.5 cm×2.5 cm, 400 mm, H426-22, Medikinetics) was fixed between the Franz cell donor compartment and receptor compartment so that the stratum corneum faced up. Then, the receptor compartment was filled with saline. Thereafter, the donor compartment was treated with FITC-EGF, a mixture of FITC-EGF and ACP, or a mixture of FITC-EGF and Transkin, and then incubated at 32° C. for 24 hours. Minipig skin tissue was fixed with 4% paraformaldehyde for 1 hour, and placed in 30% sucrose until the skin tissue was settled. The skin tissue was frozen with OCT compound (Leica, Germany) and sectioned with a cryostat microtome, thus preparing skin tissue section slides. The slides were stained with DAPI for 10 minutes, and then observed by confocal laser scanning microscopy.

Figure 15:
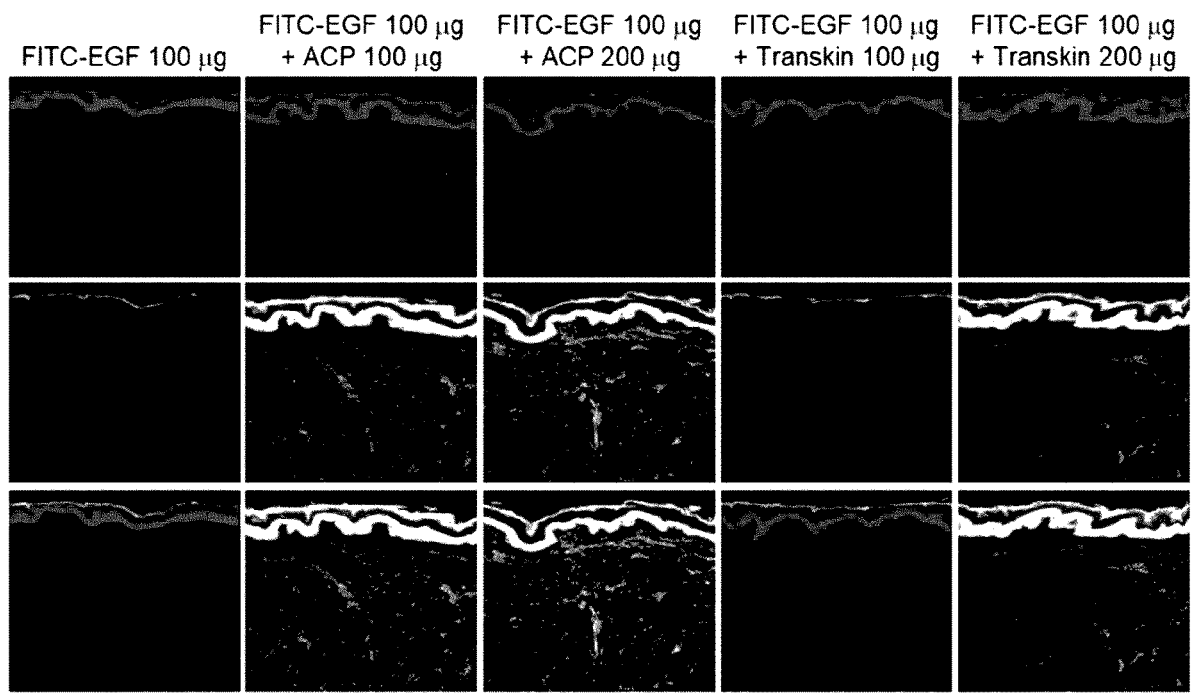
FIG. 15 shows the results of analyzing the effects of FITC-EGF, FITC-EGF+ACP and FITC-EGF+Transkin peptide on penetration into minipig skin tissue in a concentration-dependent manner.

As a result, it could be confirmed that the mixture of EGF and ACP had skin-penetrating activity, and when compared with the Transkin mixture having the same concentration (100 μg), the ACP mixture penetrated the skin, whereas the Transkin mixture did not penetrate the skin, suggesting that the ACP mixture exhibited a significant skin-penetrating effect (FIG. 15).

5-4. Analysis of Whether Mixture of Cell-Penetrating Peptide and Epidermal Growth Factor Increases Cell Migration in In Vitro Wound Healing Assay A431 cells were cultured in an RPMI-1640 medium (Hyclone, USA) supplemented with 10% FBS and 100 U/ml penicillin/streptomycin. The cultured A431 cells were seeded into a 24-well plate containing glass at a density of $1 \times 10^5$ cells/well, and then cultured for 24 hours. The confluent monolayer cells at the bottom were scraped with a tip, and then the culture medium was replaced with a medium containing 5% FBS and 100 U/ml penicillin/streptomycin. The concentration of EGF was fixed to 50 ng, and 5 nM, 10 nM and 30 nM of ACP or ACP2 were mixed with EGF. The cells were treated with each of the mixtures, and a positive control group was treated with 50 mg/ml of recombinant human EGF. Thereafter, the cells were additionally cultured for 18 hours, and then migration of the cells was observed under a microscope.

Figure 16:
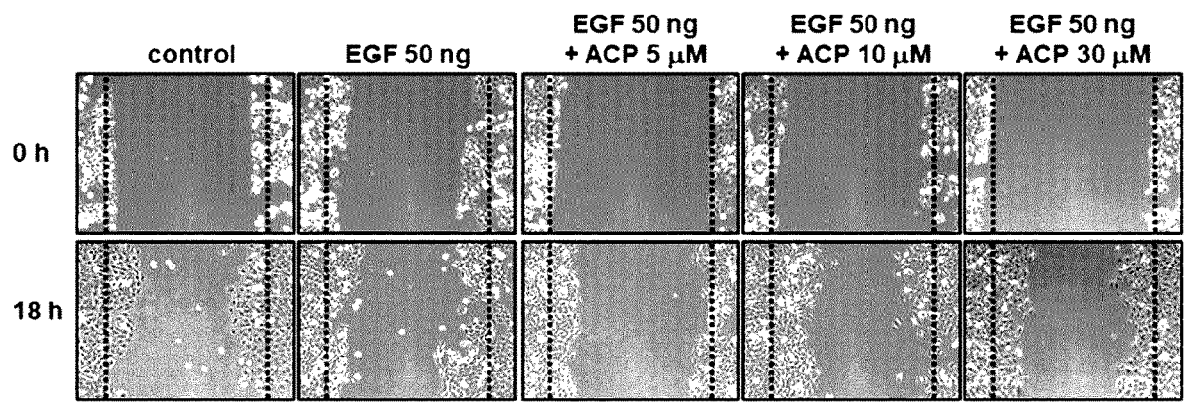
FIG. 16 shows the results of analyzing the effect of ACP+EGF (mixture) on increased cell migration in A431 cells.
Figure 16:
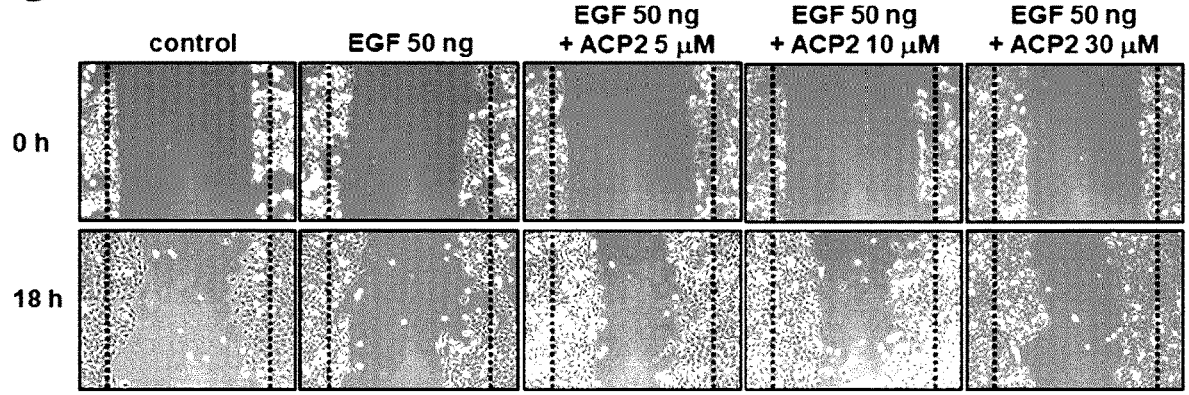

As a result, it could be confirmed that the mixture of recombinant human EGF and ACP or ACP2 significantly increased cell migration compared to the positive control group (EGF 50 ng/ml) (FIG. 16).

The present disclosure has been described above with reference to the embodiments. Those skilled in the art to which the present disclosure pertains will appreciate that the present disclosure may be embodied in modified forms without departing from the essential characteristics of the present disclosure. Therefore, it should be understood that the disclosed embodiments are illustrative in all aspects and are not restrictive. The scope of the present disclosure is defined by the claims rather than the foregoing description, and all differences within the scope equivalent to the claims should be construed as falling within the scope of the present disclosure.

The invention claimed is:

1. A conjugate comprising: a physiologically active molecule; and a cell-penetrating peptide comprising the amino acid sequence selected from the group consisting of SEQ ID NOs: 1 to 3, wherein the physiologically active molecule is the polypeptide selected from the group consisting of SEQ ID NOs: 4 to 6.

2. A cosmetic composition for skin condition improvement, the cosmetic composition comprising, as an active ingredient, the conjugate of claim 1.

3. The cosmetic composition of claim 2, wherein the cosmetic composition is a formulation selected from the group consisting of emulsion, cream, essence, skin lotion, liposomes, microcapsules, composite particles, shampoo, and rinse.

4. A pharmaceutical composition for wrinkle reduction, muscle stiffness relief or skin wound healing, the pharmaceutical composition comprising, as an active ingredient, the conjugate of claim 1.

5. A method for wrinkle reduction, muscle stiffness relief or skin wound healing, the method comprising a step of administering the composition of claim 4 to a subject.

* * * * *

SEQUENCE LISTING

<160> NUMBER OF SEQ ID NOS: 36

<210> SEQ ID NO 1
<211> LENGTH: 55
<212> TYPE: PRT
<213> ORGANISM: Artificial Sequence
<220> FEATURE:
<223> OTHER INFORMATION: ACP amino acids

<400> SEQUENCE: 1

Met Gln Arg Gly Asn Phe Arg Asn Gln Arg Lys Ile Val Lys Cys Phe
1               5                   10                  15

Asn Cys Gly Lys Glu Gly His Thr Ala Arg Asn Cys Arg Ala Pro Arg
            20                  25                  30

```
Lys Lys Gly Cys Trp Lys Cys Lys Glu Gly His Gln Met Lys Asp
        35                  40                  45

Cys Thr Glu Arg Gln Ala Asn
    50                  55

<210> SEQ ID NO 2
<211> LENGTH: 23
<212> TYPE: PRT
<213> ORGANISM: Artificial Sequence
<220> FEATURE:
<223> OTHER INFORMATION: ACP2 amino acids

<400> SEQUENCE: 2

Val Lys Cys Phe Asn Cys Gly Lys Glu Gly His Thr Ala Arg Asn Cys
1               5                   10                  15

Arg Ala Pro Arg Lys Lys Gly
            20

<210> SEQ ID NO 3
<211> LENGTH: 39
<212> TYPE: PRT
<213> ORGANISM: Artificial Sequence
<220> FEATURE:
<223> OTHER INFORMATION: ACP1 amino acids

<400> SEQUENCE: 3

Val Lys Cys Phe Asn Cys Gly Lys Glu Gly His Thr Ala Arg Asn Cys
1               5                   10                  15

Arg Ala Pro Arg Lys Lys Gly Cys Trp Lys Cys Gly Lys Glu Gly His
            20                  25                  30

Gln Met Lys Asp Cys Thr Glu
            35

<210> SEQ ID NO 4
<211> LENGTH: 446
<212> TYPE: PRT
<213> ORGANISM: Artificial Sequence
<220> FEATURE:
<223> OTHER INFORMATION: botulinum toxin amino acids

<400> SEQUENCE: 4

Pro Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
            20                  25                  30

Lys Ala Phe Lys Ile His Asn Lys Ile Trp Val Ile Pro Glu Arg Asp
        35                  40                  45

Thr Phe Thr Asn Pro Glu Glu Gly Asp Leu Asn Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Tyr Leu Lys Gly Val Thr Lys Leu Phe Glu Arg Ile
                85                  90                  95

Tyr Ser Thr Asp Leu Gly Arg Met Leu Leu Thr Ser Ile Val Arg Gly
            100                 105                 110

Ile Pro Phe Trp Gly Gly Ser Thr Ile Asp Thr Glu Leu Lys Val Ile
        115                 120                 125

Asp Thr Asn Cys Ile Asn Val Ile Gln Pro Asp Gly Ser Tyr Arg Ser
    130                 135                 140
```

```
Glu Glu Leu Asn Leu Val Ile Ile Gly Pro Ser Ala Asp Ile Ile Gln
145                 150                 155                 160

Phe Glu Cys Lys Ser Phe Gly His Glu Val Leu Asn Leu Thr Arg Asn
                165                 170                 175

Gly Tyr Gly Ser Thr Gln Tyr Ile Arg Phe Ser Pro Asp Phe Thr Phe
            180                 185                 190

Gly Phe Glu Glu Ser Leu Glu Val Asp Thr Asn Pro Leu Leu Gly Ala
        195                 200                 205

Gly Lys Phe Ala Thr Asp Pro Ala Val Thr Leu Ala His Glu Leu Ile
    210                 215                 220

His Ala Gly His Arg Leu Tyr Gly Ile Ala Ile Asn Pro Asn Arg Val
225                 230                 235                 240

Phe Lys Val Asn Thr Asn Ala Tyr Tyr Glu Met Ser Gly Leu Glu Val
                245                 250                 255

Ser Phe Glu Glu Leu Arg Thr Phe Gly Gly His Asp Ala Lys Phe Ile
                260                 265                 270

Asp Ser Leu Gln Glu Asn Glu Phe Arg Leu Tyr Tyr Asn Lys Phe
            275                 280                 285

Lys Asp Ile Ala Ser Thr Leu Asn Lys Ala Lys Ser Ile Val Gly Thr
    290                 295                 300

Thr Ala Ser Leu Gln Tyr Met Lys Asn Val Phe Lys Glu Lys Tyr Leu
305                 310                 315                 320

Leu Ser Glu Asp Thr Ser Gly Lys Phe Ser Val Asp Lys Leu Lys Phe
                325                 330                 335

Asp Lys Leu Tyr Lys Met Leu Thr Glu Ile Tyr Thr Glu Asp Asn Phe
            340                 345                 350

Val Lys Phe Phe Lys Val Leu Asn Arg Lys Thr Tyr Leu Asn Phe Asp
        355                 360                 365

Lys Ala Val Phe Lys Ile Asn Ile Val Pro Lys Val Asn Tyr Thr Ile
    370                 375                 380

Tyr Asp Gly Phe Asn Leu Arg Asn Thr Asn Leu Ala Ala Asn Phe Asn
385                 390                 395                 400

Gly Gln Asn Thr Glu Ile Asn Asn Met Asn Phe Thr Lys Leu Lys Asn
                405                 410                 415

Phe Thr Gly Leu Phe Glu Phe Tyr Lys Leu Leu Cys Val Arg Gly Ile
                420                 425                 430

Ile Thr Ser Lys Thr Lys Ser Leu Asp Lys Gly Tyr Asn Lys
            435                 440                 445

<210> SEQ ID NO 5
<211> LENGTH: 53
<212> TYPE: PRT
<213> ORGANISM: Artificial Sequence
<220> FEATURE:
<223> OTHER INFORMATION: EGF amino acids

<400> SEQUENCE: 5

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

-continued

```
<210> SEQ ID NO 6
<211> LENGTH: 6
<212> TYPE: PRT
<213> ORGANISM: Artificial Sequence
<220> FEATURE:
<223> OTHER INFORMATION: hexapeptide amino acids

<400> SEQUENCE: 6

Glu Glu Met Gln Arg Arg
1               5

<210> SEQ ID NO 7
<211> LENGTH: 506
<212> TYPE: PRT
<213> ORGANISM: Artificial Sequence
<220> FEATURE:
<223> OTHER INFORMATION: ACP-BTLC amino acids

<400> SEQUENCE: 7

Met Gly Gln Arg Gly Asn Phe Arg Asn Gln Arg Lys Thr Val Lys Cys
1               5                   10                  15

Phe Asn Cys Gly Lys Glu Gly His Ile Ala Lys Asn Cys Arg Ala Pro
            20                  25                  30

Arg Lys Lys Gly Cys Trp Arg Cys Gly Arg Glu Gly His Gln Met Lys
        35                  40                  45

Asp Cys Thr Glu Arg Gln Ala Asn Leu Thr Ser Leu Pro Phe Val Asn
    50                  55                  60

Lys Gln Phe Asn Tyr Lys Asp Pro Val Asn Gly Val Asp Ile Ala Tyr
65                  70                  75                  80

Ile Lys Ile Pro Asn Ala Gly Gln Met Gln Pro Val Lys Ala Phe Lys
                85                  90                  95

Ile His Asn Lys Ile Trp Val Ile Pro Glu Arg Asp Thr Phe Thr Asn
            100                 105                 110

Pro Glu Glu Gly Asp Leu Asn Pro Pro Glu Ala Lys Gln Val Pro
        115                 120                 125

Val Ser Tyr Tyr Asp Ser Thr Tyr Leu Ser Thr Asp Asn Glu Lys Asp
    130                 135                 140

Tyr Leu Lys Gly Val Thr Lys Leu Phe Glu Arg Ile Tyr Ser Thr Asp
145                 150                 155                 160

Leu Gly Arg Met Leu Leu Thr Ser Ile Val Arg Gly Ile Pro Phe Trp
                165                 170                 175

Gly Gly Ser Thr Ile Asp Thr Glu Leu Lys Val Ile Asp Thr Asn Cys
            180                 185                 190

Ile Asn Val Ile Gln Pro Asp Gly Ser Tyr Arg Ser Glu Glu Leu Asn
        195                 200                 205

Leu Val Ile Ile Gly Pro Ser Ala Asp Ile Ile Gln Phe Glu Cys Lys
    210                 215                 220

Ser Phe Gly His Glu Val Leu Asn Leu Thr Arg Asn Gly Tyr Gly Ser
225                 230                 235                 240

Thr Gln Tyr Ile Arg Phe Ser Pro Asp Phe Thr Phe Gly Phe Glu Glu
                245                 250                 255

Ser Leu Glu Val Asp Thr Asn Pro Leu Leu Gly Ala Gly Lys Phe Ala
            260                 265                 270

Thr Asp Pro Ala Val Thr Leu Ala His Glu Leu Ile His Ala Gly His
        275                 280                 285

Arg Leu Tyr Gly Ile Ala Ile Asn Pro Asn Arg Val Phe Lys Val Asn
    290                 295                 300
```

```
Thr Asn Ala Tyr Tyr Glu Met Ser Gly Leu Glu Val Ser Phe Glu Glu
305                 310                 315                 320

Leu Arg Thr Phe Gly Gly His Asp Ala Lys Phe Ile Asp Ser Leu Gln
            325                 330                 335

Glu Asn Glu Phe Arg Leu Tyr Tyr Asn Lys Phe Lys Asp Ile Ala
        340                 345                 350

Ser Thr Leu Asn Lys Ala Lys Ser Ile Val Gly Thr Thr Ala Ser Leu
        355                 360                 365

Gln Tyr Met Lys Asn Val Phe Lys Glu Lys Tyr Leu Leu Ser Glu Asp
    370                 375                 380

Thr Ser Gly Lys Phe Ser Val Asp Lys Leu Lys Phe Asp Lys Leu Tyr
385                 390                 395                 400

Lys Met Leu Thr Glu Ile Tyr Thr Glu Asp Asn Phe Val Lys Phe Phe
            405                 410                 415

Lys Val Leu Asn Arg Lys Thr Tyr Leu Asn Phe Asp Lys Ala Val Phe
            420                 425                 430

Lys Ile Asn Ile Val Pro Lys Val Asn Tyr Thr Ile Tyr Asp Gly Phe
            435                 440                 445

Asn Leu Arg Asn Thr Asn Leu Ala Ala Asn Phe Asn Gly Gln Asn Thr
450                 455                 460

Glu Ile Asn Asn Met Asn Phe Thr Lys Leu Lys Asn Phe Thr Gly Leu
465                 470                 475                 480

Phe Glu Phe Tyr Lys Leu Leu Cys Val Arg Gly Ile Ile Thr Ser Lys
            485                 490                 495

Thr Lys Ser Leu Asp Lys Gly Tyr Asn Lys
            500                 505

<210> SEQ ID NO 8
<211> LENGTH: 472
<212> TYPE: PRT
<213> ORGANISM: Artificial Sequence
<220> FEATURE:
<223> OTHER INFORMATION: ACP2-BTLC amino acids

<400> SEQUENCE: 8

Met Lys Cys Phe Asn Cys Gly Lys Glu Gly His Ile Ala Lys Asn Cys
1               5                   10                  15

Arg Ala Pro Arg Lys Lys Gly Lys Leu Pro Phe Val Asn Lys Gln Phe
            20                  25                  30

Asn Tyr Lys Asp Pro Val Asn Gly Val Asp Ile Ala Tyr Ile Lys Ile
        35                  40                  45

Pro Asn Ala Gly Gln Met Gln Pro Val Lys Ala Phe Lys Ile His Asn
    50                  55                  60

Lys Ile Trp Val Ile Pro Glu Arg Asp Thr Phe Thr Asn Pro Glu Glu
65                  70                  75                  80

Gly Asp Leu Asn Pro Pro Glu Ala Lys Gln Val Pro Val Ser Tyr
            85                  90                  95

Tyr Asp Ser Thr Tyr Leu Ser Thr Asp Asn Glu Lys Asp Asn Tyr Leu
            100                 105                 110

Lys Gly Val Thr Lys Leu Phe Glu Arg Ile Tyr Ser Thr Asp Leu Gly
        115                 120                 125

Arg Met Leu Leu Thr Ser Ile Val Arg Gly Ile Pro Phe Trp Gly Gly
    130                 135                 140

Ser Thr Ile Asp Thr Glu Leu Lys Val Ile Asp Thr Asn Cys Ile Asn
145                 150                 155                 160
```

-continued

```
Val Ile Gln Pro Asp Gly Ser Tyr Arg Ser Glu Glu Leu Asn Leu Val
            165                 170                 175

Ile Ile Gly Pro Ser Ala Asp Ile Ile Gln Phe Glu Cys Lys Ser Phe
        180                 185                 190

Gly His Glu Val Leu Asn Leu Thr Arg Asn Gly Tyr Gly Ser Thr Gln
        195                 200                 205

Tyr Ile Arg Phe Ser Pro Asp Phe Thr Phe Gly Phe Glu Glu Ser Leu
        210                 215                 220

Glu Val Asp Thr Asn Pro Leu Leu Gly Ala Gly Lys Phe Ala Thr Asp
225                 230                 235                 240

Pro Ala Val Thr Leu Ala His Glu Leu Ile His Ala Gly His Arg Leu
                245                 250                 255

Tyr Gly Ile Ala Ile Asn Pro Asn Arg Val Phe Lys Val Asn Thr Asn
            260                 265                 270

Ala Tyr Tyr Glu Met Ser Gly Leu Glu Val Ser Phe Glu Glu Leu Arg
        275                 280                 285

Thr Phe Gly Gly His Asp Ala Lys Phe Ile Asp Ser Leu Gln Glu Asn
        290                 295                 300

Glu Phe Arg Leu Tyr Tyr Tyr Asn Lys Phe Lys Asp Ile Ala Ser Thr
305                 310                 315                 320

Leu Asn Lys Ala Lys Ser Ile Val Gly Thr Thr Ala Ser Leu Gln Tyr
                325                 330                 335

Met Lys Asn Val Phe Lys Glu Lys Tyr Leu Leu Ser Glu Asp Thr Ser
            340                 345                 350

Gly Lys Phe Ser Val Asp Lys Leu Lys Phe Asp Lys Leu Tyr Lys Met
        355                 360                 365

Leu Thr Glu Ile Tyr Thr Glu Asp Asn Phe Val Lys Phe Phe Lys Val
370                 375                 380

Leu Asn Arg Lys Thr Tyr Leu Asn Phe Asp Lys Ala Val Phe Lys Ile
385                 390                 395                 400

Asn Ile Val Pro Lys Val Asn Tyr Thr Ile Tyr Asp Gly Phe Asn Leu
                405                 410                 415

Arg Asn Thr Asn Leu Ala Ala Asn Phe Asn Gly Gln Asn Thr Glu Ile
            420                 425                 430

Asn Asn Met Asn Phe Thr Lys Leu Lys Asn Phe Thr Gly Leu Phe Glu
        435                 440                 445

Phe Tyr Lys Leu Leu Cys Val Arg Gly Ile Ile Thr Ser Lys Thr Lys
        450                 455                 460

Ser Leu Asp Lys Gly Tyr Asn Lys
465                 470
```

<210> SEQ ID NO 9
<211> LENGTH: 488
<212> TYPE: PRT
<213> ORGANISM: Artificial Sequence
<220> FEATURE:
<223> OTHER INFORMATION: ACP1-BTLC amino acids

<400> SEQUENCE: 9

```
Met Lys Cys Phe Asn Cys Gly Lys Glu Gly His Ile Ala Lys Asn Cys
1               5                   10                  15

Arg Ala Pro Arg Lys Lys Gly Cys Trp Arg Cys Gly Arg Glu Gly His
            20                  25                  30

Gln Met Lys Asp Cys Thr Glu Lys Leu Pro Phe Val Asn Lys Gln Phe
        35                  40                  45
```

```
Asn Tyr Lys Asp Pro Val Asn Gly Val Asp Ile Ala Tyr Ile Lys Ile
        50                  55                  60

Pro Asn Ala Gly Gln Met Gln Pro Val Lys Ala Phe Lys Ile His Asn
 65                  70                  75                  80

Lys Ile Trp Val Ile Pro Glu Arg Asp Thr Phe Thr Asn Pro Glu Glu
                 85                  90                  95

Gly Asp Leu Asn Pro Pro Glu Ala Lys Gln Val Pro Val Ser Tyr
            100                 105                 110

Tyr Asp Ser Thr Tyr Leu Ser Thr Asp Asn Glu Lys Asp Asn Tyr Leu
            115                 120                 125

Lys Gly Val Thr Lys Leu Phe Glu Arg Ile Tyr Ser Thr Asp Leu Gly
        130                 135                 140

Arg Met Leu Leu Thr Ser Ile Val Arg Gly Ile Pro Phe Trp Gly Gly
145                 150                 155                 160

Ser Thr Ile Asp Thr Glu Leu Lys Val Ile Asp Thr Asn Cys Ile Asn
                165                 170                 175

Val Ile Gln Pro Asp Gly Ser Tyr Arg Ser Glu Glu Leu Asn Leu Val
            180                 185                 190

Ile Ile Gly Pro Ser Ala Asp Ile Ile Gln Phe Glu Cys Lys Ser Phe
        195                 200                 205

Gly His Glu Val Leu Asn Leu Thr Arg Asn Gly Tyr Gly Ser Thr Gln
        210                 215                 220

Tyr Ile Arg Phe Ser Pro Asp Phe Thr Phe Gly Phe Glu Glu Ser Leu
225                 230                 235                 240

Glu Val Asp Thr Asn Pro Leu Leu Gly Ala Gly Lys Phe Ala Thr Asp
                245                 250                 255

Pro Ala Val Thr Leu Ala His Glu Leu Ile His Ala Gly His Arg Leu
            260                 265                 270

Tyr Gly Ile Ala Ile Asn Pro Asn Arg Val Phe Lys Val Asn Thr Asn
        275                 280                 285

Ala Tyr Tyr Glu Met Ser Gly Leu Glu Val Ser Phe Glu Glu Leu Arg
290                 295                 300

Thr Phe Gly Gly His Asp Ala Lys Phe Ile Asp Ser Leu Gln Glu Asn
305                 310                 315                 320

Glu Phe Arg Leu Tyr Tyr Tyr Asn Lys Phe Lys Asp Ile Ala Ser Thr
                325                 330                 335

Leu Asn Lys Ala Lys Ser Ile Val Gly Thr Thr Ala Ser Leu Gln Tyr
            340                 345                 350

Met Lys Asn Val Phe Lys Glu Lys Tyr Leu Leu Ser Glu Asp Thr Ser
        355                 360                 365

Gly Lys Phe Ser Val Asp Lys Leu Lys Phe Asp Lys Leu Tyr Lys Met
        370                 375                 380

Leu Thr Glu Ile Tyr Thr Glu Asp Asn Phe Val Lys Phe Phe Lys Val
385                 390                 395                 400

Leu Asn Arg Lys Thr Tyr Leu Asn Phe Asp Lys Ala Val Phe Lys Ile
                405                 410                 415

Asn Ile Val Pro Lys Val Asn Tyr Thr Ile Tyr Asp Gly Phe Asn Leu
            420                 425                 430

Arg Asn Thr Asn Leu Ala Ala Asn Phe Asn Gly Gln Asn Thr Glu Ile
        435                 440                 445

Asn Asn Met Asn Phe Thr Lys Leu Lys Asn Phe Thr Gly Leu Phe Glu
450                 455                 460
```

```
Phe Tyr Lys Leu Leu Cys Val Arg Gly Ile Ile Thr Ser Lys Thr Lys
465                 470                 475                 480

Ser Leu Asp Lys Gly Tyr Asn Lys
                485

<210> SEQ ID NO 10
<211> LENGTH: 503
<212> TYPE: PRT
<213> ORGANISM: Artificial Sequence
<220> FEATURE:
<223> OTHER INFORMATION: BTLC-ACP amino acids

<400> SEQUENCE: 10

Pro Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
                20                  25                  30

Lys Ala Phe Lys Ile His Asn Lys Ile Trp Val Ile Pro Glu Arg Asp
            35                  40                  45

Thr Phe Thr Asn Pro Glu Glu Gly Asp Leu Asn Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Tyr Leu Lys Gly Val Thr Lys Leu Phe Glu Arg Ile
                85                  90                  95

Tyr Ser Thr Asp Leu Gly Arg Met Leu Leu Thr Ser Ile Val Arg Gly
                100                 105                 110

Ile Pro Phe Trp Gly Gly Ser Thr Ile Asp Thr Glu Leu Lys Val Ile
            115                 120                 125

Asp Thr Asn Cys Ile Asn Val Ile Gln Pro Asp Gly Ser Tyr Arg Ser
130                 135                 140

Glu Glu Leu Asn Leu Val Ile Ile Gly Pro Ser Ala Asp Ile Ile Gln
145                 150                 155                 160

Phe Glu Cys Lys Ser Phe Gly His Glu Val Leu Asn Leu Thr Arg Asn
                165                 170                 175

Gly Tyr Gly Ser Thr Gln Tyr Ile Arg Phe Ser Pro Asp Phe Thr Phe
                180                 185                 190

Gly Phe Glu Glu Ser Leu Glu Val Asp Thr Asn Pro Leu Leu Gly Ala
            195                 200                 205

Gly Lys Phe Ala Thr Asp Pro Ala Val Thr Leu Ala His Glu Leu Ile
210                 215                 220

His Ala Gly His Arg Leu Tyr Gly Ile Ala Ile Asn Pro Asn Arg Val
225                 230                 235                 240

Phe Lys Val Asn Thr Asn Ala Tyr Tyr Glu Met Ser Gly Leu Glu Val
                245                 250                 255

Ser Phe Glu Glu Leu Arg Thr Phe Gly Gly His Asp Ala Lys Phe Ile
                260                 265                 270

Asp Ser Leu Gln Glu Asn Glu Phe Arg Leu Tyr Tyr Tyr Asn Lys Phe
            275                 280                 285

Lys Asp Ile Ala Ser Thr Leu Asn Lys Ala Lys Ser Ile Val Gly Thr
290                 295                 300

Thr Ala Ser Leu Gln Tyr Met Lys Asn Val Phe Lys Glu Lys Tyr Leu
305                 310                 315                 320

Leu Ser Glu Asp Thr Ser Gly Lys Phe Ser Val Asp Lys Leu Lys Phe
                325                 330                 335
```

Asp Lys Leu Tyr Lys Met Leu Thr Glu Ile Tyr Thr Glu Asp Asn Phe
                340                 345                 350

Val Lys Phe Phe Lys Val Leu Asn Arg Lys Thr Tyr Leu Asn Phe Asp
        355                 360                 365

Lys Ala Val Phe Lys Ile Asn Ile Val Pro Lys Val Asn Tyr Thr Ile
    370                 375                 380

Tyr Asp Gly Phe Asn Leu Arg Asn Thr Asn Leu Ala Ala Asn Phe Asn
385                 390                 395                 400

Gly Gln Asn Thr Glu Ile Asn Asn Met Asn Phe Thr Lys Leu Lys Asn
                405                 410                 415

Phe Thr Gly Leu Phe Glu Phe Tyr Lys Leu Leu Cys Val Arg Gly Ile
        420                 425                 430

Ile Thr Ser Lys Thr Lys Ser Leu Asp Lys Gly Tyr Asn Lys Lys Leu
    435                 440                 445

Met Gln Arg Gly Asn Phe Arg Asn Gln Arg Lys Ile Val Lys Cys Phe
    450                 455                 460

Asn Cys Gly Lys Glu Gly His Thr Ala Arg Asn Cys Arg Ala Pro Arg
465                 470                 475                 480

Lys Lys Gly Cys Trp Lys Cys Gly Lys Glu Gly His Gln Met Lys Asp
                485                 490                 495

Cys Thr Glu Arg Gln Ala Asn
            500

<210> SEQ ID NO 11
<211> LENGTH: 76
<212> TYPE: PRT
<213> ORGANISM: Artificial Sequence
<220> FEATURE:
<223> OTHER INFORMATION: ACP2-EGF amino acids

<400> SEQUENCE: 11

Val Lys Cys Phe Asn Cys Gly Lys Glu Gly His Ile Ala Lys Asn Cys
1               5                   10                  15

Arg Ala Pro Arg Lys Lys Gly Asn Ser Asp Ser Glu Cys Pro Leu Ser
            20                  25                  30

His Asp Gly Tyr Cys Leu His Asp Gly Val Cys Met Tyr Ile Glu Ala
        35                  40                  45

Leu Asp Lys Tyr Ala Cys Asn Cys Val Val Gly Tyr Ile Gly Glu Arg
    50                  55                  60

Cys Gln Tyr Arg Asp Leu Lys Trp Trp Glu Leu Arg
65                  70                  75

<210> SEQ ID NO 12
<211> LENGTH: 45
<212> TYPE: PRT
<213> ORGANISM: Artificial Sequence
<220> FEATURE:
<223> OTHER INFORMATION: ACP2-hexapeptide amino acids

<400> SEQUENCE: 12

Val Lys Cys Phe Asn Cys Gly Lys Glu Gly His Thr Ala Arg Asn Cys
1               5                   10                  15

Arg Ala Pro Arg Lys Lys Gly Cys Trp Lys Cys Gly Lys Glu Gly His
            20                  25                  30

Gln Met Lys Asp Cys Thr Glu Glu Met Gln Arg Arg
        35                  40                  45

<210> SEQ ID NO 13
<211> LENGTH: 165
<212> TYPE: DNA
<213> ORGANISM: Artificial Sequence
<220> FEATURE:
<223> OTHER INFORMATION: ACP polynucleotides

<400> SEQUENCE: 13

```
atgcagcgcg gcaactttcg caaccagcgc aaaattgtga atgctttaa ctgcggcaaa      60 gaaggccata ccgcgcgcaa ctgccgcgcg ccgcgcaaaa aaggctgctg gaaatgcggc     120
aaagaaggcc atcagatgaa agattgcacc gaacgccagg cgaac                    165
```

<210> SEQ ID NO 14
<211> LENGTH: 75
<212> TYPE: DNA
<213> ORGANISM: Artificial Sequence
<220> FEATURE:
<223> OTHER INFORMATION: ACP2 polynucleotides

<400> SEQUENCE: 14

```
atgaagtgct tcaattgcgg aaaggagggc cacatcgcta agaactgccg cgcccccaga      60
aagaaaggca agctt                                                      75
```

<210> SEQ ID NO 15
<211> LENGTH: 117
<212> TYPE: DNA
<213> ORGANISM: Artificial Sequence
<220> FEATURE:
<223> OTHER INFORMATION: ACP1 polynucleotides

<400> SEQUENCE: 15

```
atgaagtgct tcaattgcgg aaaggagggc cacatcgcta agaactgccg cgcccccaga      60
aagaaaggct gctggagatg cggcagagag ggccaccaga tgaaggactg cacagag        117
```

<210> SEQ ID NO 16
<211> LENGTH: 1341
<212> TYPE: DNA
<213> ORGANISM: Artificial Sequence
<220> FEATURE:
<223> OTHER INFORMATION: BTLC polynucleotides

<400> SEQUENCE: 16

```
ccgttcgtta caaacagtt caactacaaa gacccggtta acggcgttga catcgcttac       60
atcaaaatcc cgaacgctgg ccagatgcag ccggttaaag cattcaagat ccacaacaaa    120
atctgggtaa tcccggaacg tgacaccttc accaacccgg aagaaggcga cctgaacccg    180
ccgccggaag ctaaacaggt tccggttttcc tactacgact ccacctacct gagcaccgac   240
aacgagaagg acaactacct gaaaggcgtt accaaactgt tcgaacgtat ctactccacc   300
gacctgggcc gtatgctgct gacctccatc gttcgtggca tcccgttctg gggcggtagc   360
accatcgaca ccgaactgaa agttatcgac accaactgca tcaacgttat ccagccggac   420
ggctcctacc gttccgaaga actgaacctg gttatcatcg gcccgtccgc tgacatcatc   480
cagttcgaat gcaaatcctt cggccacgaa gttctgaacc tgacccgtaa cggctacggc   540 tccaccccagt acatccgttt ctcccccggac ttcaccttcg gcttcgaaga atccctggaa   600
gttgacacca cccgctgctg gggcgctggc aaattcgcta ccgacccggc tgttaccctg   660
gctcacgaac tgatccacgc tggccaccgt ctgtacggca tcgctatcaa cccgaaccgt   720
gttttcaaag ttaacaccaa cgcttactac gaaatgtccg gcctggaagt ttccttcgaa   780
```

| | |
|---|---|
| gaactgcgta ccttcggcgg ccacgacgct aaattcatcg actccctgca ggagaacgaa | 840 |
| ttccgtctgt actattacaa caaattcaaa gacatcgctt ccaccctgaa caaagctaaa | 900 |
| tccatcgttg gcaccaccgc ttccctgcag tacatgaaga acgttttcaa agagaagtac | 960 |
| ctgctgtccg aagacacctc cggcaaattc tccgttgaca aactgaaatt cgacaaactg | 1020 |
| tacaagatgc tgaccgaaat ctacaccgaa gacaacttcg ttaaattctt caaagttctg | 1080 |
| aaccgtaaaa cctacctgaa cttcgacaaa gctgttttca agatcaacat cgttccgaaa | 1140 |
| gttaactaca ccatctacga cggcttcaac ctgcgtaaca ccaacctggc tgctaacttc | 1200 |
| aacggccaga acaccgaaat caacaacatg aacttcacca aactgaagaa cttcaccggc | 1260 |
| ctgttcgaat tctacaaact gctgtgcgtt cgtggcatca tcacctccaa aaccaaatcc | 1320 |
| ctggacaaag gctacaacaa a | 1341 |

<210> SEQ ID NO 17
<211> LENGTH: 159
<212> TYPE: DNA
<213> ORGANISM: Artificial Sequence
<220> FEATURE:
<223> OTHER INFORMATION: EGF polynucleotides

<400> SEQUENCE: 17

| | |
|---|---|
| aattctgata gcgagtgtcc gctgagtcac gacggttatt gtctgcacga cggcgtttgt | 60 |
| atgtacatcg aagcgctgga caaatacgcc tgcaattgcg tagtcggcta tatcggcgaa | 120 |
| cgttgtcagt atcgcgacct gaaatggtgg gaactgcgt | 159 |

<210> SEQ ID NO 18
<211> LENGTH: 18
<212> TYPE: DNA
<213> ORGANISM: Artificial Sequence
<220> FEATURE:
<223> OTHER INFORMATION: hexapeptide polynucleotides

<400> SEQUENCE: 18

| | |
|---|---|
| gaagaaatgc agcgccgc | 18 |

<210> SEQ ID NO 19
<211> LENGTH: 1521
<212> TYPE: DNA
<213> ORGANISM: Artificial Sequence
<220> FEATURE:
<223> OTHER INFORMATION: ACP-BTLC polynucleotides

<400> SEQUENCE: 19

| | |
|---|---|
| atgggccagc ggggaaactt caggaaccag agaaaaactg tgaagtgctt caattgcgga | 60 |
| aaggagggcc acatcgctaa gaactgccgc gcccccagaa agaaaggctg ctggagatgc | 120 |
| ggcagagagg gccaccagat gaaggactgc acagagagac aggcaaactt aacaagcttg | 180 |
| ccgttcgtta acaaacagtt caactacaaa gacccggtta acggcgttga catcgcttac | 240 |
| atcaaaatcc cgaacgctgg ccagatgcag ccggttaaag cattcaagat ccacaacaaa | 300 |
| atctgggtaa tcccggaacg tgacaccttc accaacccgg aagaaggcga cctgaacccg | 360 |
| ccgccggaag ctaaacaggt tccggttttcc tactacgact ccacctacct gagcaccgac | 420 |
| aacgagaagg acaactacct gaaaggcgtt accaaactgt cgaacgtat ctactccacc | 480 |
| gacctgggcc gtatgctgct gacctccatc gttcgtggca tccgttctctg gggcggtagc | 540 |
| accatcgaca ccgaactgaa agttatcgac accaactgca tcaacgttat ccagccggac | 600 |
| ggctcctacc gttccgaaga actgaacctg gttatcatcg gcccgtccgc tgacatcatc | 660 |

| | |
|---|---|
| cagttcgaat gcaaatcctt cggccacgaa gttctgaacc tgacccgtaa cggctacggc | 720 |
| tccacccagt acatccgttt ctccccggac ttcaccttcg gcttcgaaga atccctggaa | 780 |
| gttgacacca acccgctgct gggcgctggc aaattcgcta ccgacccggc tgttaccctg | 840 |
| gctcacgaac tgatccacgc tggccaccgt ctgtacggca tcgctatcaa cccgaaccgt | 900 |
| gttttcaaag ttaacaccaa cgcttactac gaaatgtccg gcctggaagt tccttcgaa | 960 |
| gaactgcgta ccttcggcgg ccacgacgct aaattcatcg actccctgca ggagaacgaa | 1020 |
| ttccgtctgt actattacaa caaattcaaa gacatcgctt ccaccctgaa caaagctaaa | 1080 |
| tccatcgttg gcaccaccgc ttccctgcag tacatgaaga cgttttcaa agagaagtac | 1140 |
| ctgctgtccg aagacacctc cggcaaattc tccgttgaca aactgaaatt cgacaaactg | 1200 |
| tacaagatgc tgaccgaaat ctacaccgaa gacaacttcg ttaaattctt caaagttctg | 1260 |
| aaccgtaaaa cctacctgaa cttcgacaaa gctgttttca agatcaacat cgttccgaaa | 1320 |
| gttaactaca ccatctacga cggcttcaac ctgcgtaaca ccaacctggc tgctaacttc | 1380 |
| aacggccaga caccgaaat caacaacatg aacttcacca aactgaagaa cttcaccggc | 1440 |
| ctgttcgaat tctacaaact gctgtgcgtt cgtggcatca tcacctccaa aaccaaatcc | 1500 |
| ctggacaaag gctacaacaa a | 1521 |

<210> SEQ ID NO 20
<211> LENGTH: 1416
<212> TYPE: DNA
<213> ORGANISM: Artificial Sequence
<220> FEATURE:
<223> OTHER INFORMATION: ACP2-BTLC polynucleotides

<400> SEQUENCE: 20

| | |
|---|---|
| atgaagtgct tcaattgcgg aaaggagggc cacatcgcta agaactgccg cgcccccaga | 60 |
| aagaaaggca agcttccgtt cgttaacaaa cagttcaact acaaagaccc ggttaacggc | 120 |
| gttgacatcg cttacatcaa aatcccgaac gctggccaga tgcagccggt taaagcattc | 180 |
| aagatccaca acaaaatctg ggtaatcccg gaacgtgaca ccttcaccaa cccggaagaa | 240 |
| ggcgacctga cccgccgcc ggaagctaaa caggttccgg tttcctacta cgactccacc | 300 |
| tacctgagca ccgacaacga aggacaac tacctgaaag gcgttaccaa actgttcgaa | 360 |
| cgtatctact ccaccgacct gggccgtatg ctgctgacct ccatcgttcg tggcatcccg | 420 |
| ttctggggcg gtagcaccat cgacaccgaa ctgaaagtta tcgacaccaa ctgcatcaac | 480 |
| gttatccagc cggacggctc ctaccgttcc gaagaactga acctggttat catcggcccg | 540 |
| tccgctgaca tcatccagtt cgaatgcaaa tccttcggcc acgaagttct gaacctgacc | 600 |
| cgtaacggct acggctccac ccagtacatc cgtttctccc cggacttcac cttcggcttc | 660 |
| gaagaatccc tggaagttga caccaacccg ctgctgggcg ctggcaaatt cgctaccgac | 720 |
| ccggctgtta ccctggctca cgaactgatc cacgctggcc accgtctgta cggcatcgct | 780 |
| atcaacccga accgtgtttt caagttaac accaacgctt actacgaaat gtccggcctg | 840 |
| gaagtttcct tcgaagaact gcgtaccttc ggcggccacg acgctaaatt catcgactcc | 900 |
| ctgcaggaga acgaattccg tctgtactat tacaacaaat tcaaagacat cgcttccacc | 960 |
| ctgaacaaag ctaaatccat cgttggcacc accgcttccc tgcagtacat gaagaacgtt | 1020 |
| ttcaaagaga agtacctgct gtccgaagac acctccggca aattctccgt tgacaaactg | 1080 |
| aaattcgaca aactgtacaa gatgctgacc gaaatctaca ccgaagacaa cttcgttaaa | 1140 |
| ttcttcaaag ttctgaaccg taaaacctac ctgaacttcg acaaagctgt tttcaagatc | 1200 |

| aacatcgttc cgaaagttaa ctacaccatc tacgacggct tcaacctgcg taacaccaac | 1260 |
| ctggctgcta acttcaacgg ccagaacacc gaaatcaaca acatgaactt caccaaactg | 1320 |
| aagaacttca ccggcctgtt cgaattctac aaactgctgt gcgttcgtgg catcatcacc | 1380 |
| tccaaaacca atccctggac aaaggctac aacaaa | 1416 |

<210> SEQ ID NO 21
<211> LENGTH: 1464
<212> TYPE: DNA
<213> ORGANISM: Artificial Sequence
<220> FEATURE:
<223> OTHER INFORMATION: ACP1-BTLC polynucleotides

<400> SEQUENCE: 21

| atgaagtgct tcaattgcgg aaaggagggc cacatcgcta agaactgccg cgcccccaga | 60 |
| aagaaaggct gctggagatg cggcagagag ggccaccaga tgaaggactg cacagagaag | 120 |
| cttccgttcg ttaacaaaca gttcaactac aaagacccgg ttaacggcgt tgacatcgct | 180 |
| tacatcaaaa tcccgaacgc tggccagatg cagccggtta aagcattcaa gatccacaac | 240 |
| aaaatctggg taatcccgga acgtgacacc ttcaccaacc cggaagaagg cgacctgaac | 300 |
| ccgccgccgg aagctaaaca ggttccggtt tcctactacg actccaccta cctgagcacc | 360 |
| gacaacgaga aggacaacta cctgaaaggc gttaccaaac tgttcgaacg tatctactcc | 420 |
| accgacctgg gccgtatgct gctgacctcc atcgttcgtg gcatcccgtt ctggggcggt | 480 |
| agcaccatcg acaccgaact gaaagttatc gacaccaact gcatcaacgt tatccagccg | 540 |
| gacggctcct accgttccga agaactgaac ctggttatca tcggcccgtc cgctgacatc | 600 |
| atccagttcg aatgcaaatc cttcggccac gaagttctga acctgacccg taacggctac | 660 |
| ggctccaccc agtacatccg tttctccccg gacttcacct tcggcttcga agaatccctg | 720 |
| gaagttgaca ccaacccgct gctgggcgct ggcaaattcg ctaccgaccc ggctgttacc | 780 |
| ctggctcacg aactgatcca cgctggccac cgtctgtacg gcatcgctat caaccccgaac | 840 |
| cgtgttttca agttaacac caacgcttac tacgaaatgt ccggcctgga gtttccttc | 900 |
| gaagaactgc gtaccttcgg cggccacgac gctaaattca tcgactccct gcaggagaac | 960 |
| gaattccgtc tgtactatta caacaaattc aagacatcg cttccaccct gaacaaagct | 1020 |
| aaatccatcg ttggcaccac cgcttccctg cagtacatga gaacgttttt caaagagaag | 1080 |
| tacctgctgt ccgaagacac ctccggcaaa ttctccgttg acaaactgaa attcgacaaa | 1140 |
| ctgtacaaga tgctgaccga aatctacacc gaagacaact tcgttaaatt cttcaaagtt | 1200 |
| ctgaaccgta aaacctacct gaacttcgac aaagctgttt tcaagatcaa catcgttccg | 1260 |
| aaagttaact acaccatcta cgacggcttc aacctgcgta acaccaacct ggctgctaac | 1320 |
| ttcaacggcc agaacaccga atcaacaac atgaacttca ccaaactgaa gaacttcacc | 1380 |
| ggcctgttcg aattctacaa actgctgtgc gttcgtggca tcatcacctc caaaaccaaa | 1440 |
| tccctggaca aaggctacaa caaa | 1464 |

<210> SEQ ID NO 22
<211> LENGTH: 1512
<212> TYPE: DNA
<213> ORGANISM: Artificial Sequence
<220> FEATURE:
<223> OTHER INFORMATION: BTLC-ACP polynucleotides

<400> SEQUENCE: 22

```
ccgttcgtta acaaacagtt caactacaaa gacccggtta acggcgttga catcgcttac      60
atcaaaatcc cgaacgctgg ccagatgcag ccggttaaag cattcaagat ccacaacaaa     120
atctgggtaa tcccggaacg tgacaccttc accaacccgg aagaaggcga cctgaacccg     180
ccgccggaag ctaaacaggt tccggttttcc tactacgact ccacctacct gagcaccgac    240
aacgagaagg acaactacct gaaggcgtt accaaactgt tcgaacgtat ctactccacc      300
gacctgggcc gtatgctgct gacctccatc gttcgtggca tcccgttctg gggcggtagc    360
accatcgaca ccgaactgaa agttatcgac accaactgca tcaacgttat ccagccggac    420
ggctcctacc gttccgaaga actgaacctg gttatcatcg gcccgtccgc tgacatcatc    480
cagttcgaat gcaaatcctt cggccacgaa gttctgaacc tgacccgtaa cggctacggc    540
tccacccagt acatccgttt ctccccggac ttcaccttcg gcttcgaaga tccctggaa     600
gttgacacca cccgctgct gggcgctggc aaattcgcta ccgacccggc tgttaccctg     660
gctcacgaac tgatccacgc tggccaccgt ctgtacggca tcgctatcaa cccgaaccgt    720
gttttcaaag ttaacaccaa cgcttactac gaaatgtccg gcctggaagt ttccttcgaa    780
gaactgcgta ccttcggcgg ccacgacgct aaattcatcg actccctgca ggagaacgaa    840
ttccgtctgt actattacaa caaattcaaa gacatcgctt ccaccctgaa caaagctaaa    900
tccatcgttg gcaccaccgc ttccctgcag tacatgaaga acgtttcaa agagaagtac     960
ctgctgtccg aagacacctc cggcaaattc tccgttgaca aactgaaatt cgacaaactg    1020
tacaagatgc tgaccgaaat ctacaccgaa gacaacttcg ttaaattctt caaagttctg    1080
aaccgtaaaa cctacctgaa cttcgacaaa gctgttttca agatcaacat cgttccgaaa    1140
gttaactaca ccatctacga cggcttcaac ctgcgtaaca ccaacctggc tgctaacttc    1200
aacggccaga caccgaaat caacaacatg aacttcacca aactgaagaa cttcaccggc     1260
ctgttcgaat ctacaaaact gctgtgcgtt cgtggcatca tcacctccaa aaccaaatcc    1320
ctggacaaag ctacaacaa aaagcttatg cagcgcggca actttcgcaa ccagcgcaaa    1380
attgtgaaat gctttaactg cggcaaagaa ggccataccg cgcgcaactg ccgcgcgccg    1440
cgcaaaaaag gctgctggaa atgcggcaaa gaaggccatc agatgaaaga ttgcaccgaa    1500
cgccaggcga ac                                                         1512
```

<210> SEQ ID NO 23
<211> LENGTH: 228
<212> TYPE: DNA
<213> ORGANISM: Artificial Sequence
<220> FEATURE:
<223> OTHER INFORMATION: ACP2-EGF polynucleotides

<400> SEQUENCE: 23

```
gtgaagtgct tcaattgcgg aaaggagggc cacatcgcta agaactgccg cgcccccaga      60
aagaaaggca attctgatag cgagtgtccg ctgagtcacg acggttattg tctgcacgac     120
ggcgtttgta tgtacatcga agcgctggac aaatacgcct gcaattgcgt agtcggctat    180
atcggcgaac gttgtcagta tcgcgacctg aaatggtggg aactgcgt                  228
```

<210> SEQ ID NO 24
<211> LENGTH: 87
<212> TYPE: DNA
<213> ORGANISM: Artificial Sequence
<220> FEATURE:
<223> OTHER INFORMATION: ACP2-hexapeptide polynucleotides

```
<400> SEQUENCE: 24
gtgaagtgct tcaattgcgg aaaggagggc cacatcgcta agaactgccg cgcccccaga    60
aagaaaggcg aagaaatgca gcgccgc                                       87

<210> SEQ ID NO 25
<211> LENGTH: 24
<212> TYPE: DNA
<213> ORGANISM: Artificial Sequence
<220> FEATURE:
<223> OTHER INFORMATION: synthetic polynucletodies

<400> SEQUENCE: 25
ccatgggcca gcggggaaac cagc                                          24

<210> SEQ ID NO 26
<211> LENGTH: 31
<212> TYPE: DNA
<213> ORGANISM: Artificial Sequence
<220> FEATURE:
<223> OTHER INFORMATION: synthetic polynucletodies

<400> SEQUENCE: 26
aagcttgtta agtttgcctg tctctctgtg c                                  31

<210> SEQ ID NO 27
<211> LENGTH: 38
<212> TYPE: DNA
<213> ORGANISM: Artificial Sequence
<220> FEATURE:
<223> OTHER INFORMATION: synthetic polynucletodies

<400> SEQUENCE: 27
aagcttccgt tcgttaacaa acagttcaac tacaaaga                            38

<210> SEQ ID NO 28
<211> LENGTH: 36
<212> TYPE: DNA
<213> ORGANISM: Artificial Sequence
<220> FEATURE:
<223> OTHER INFORMATION: synthetic polynucletodies

<400> SEQUENCE: 28
ctcgagtcat tgttgtagc ctttgtccag ggattt                               36

<210> SEQ ID NO 29
<211> LENGTH: 30
<212> TYPE: DNA
<213> ORGANISM: Artificial Sequence
<220> FEATURE:
<223> OTHER INFORMATION: synthetic polynucletodies

<400> SEQUENCE: 29
catatgaagt gcttcaattg cggaaaggag                                    30

<210> SEQ ID NO 30
<211> LENGTH: 24
<212> TYPE: DNA
<213> ORGANISM: Artificial Sequence
<220> FEATURE:
<223> OTHER INFORMATION: synthetic polynucletodies

<400> SEQUENCE: 30
aagcttgcct ttctttctgg gggc                                          24
```

```
<210> SEQ ID NO 31
<211> LENGTH: 28
<212> TYPE: DNA
<213> ORGANISM: Artificial Sequence
<220> FEATURE:
<223> OTHER INFORMATION: synthetic polynucletodies

<400> SEQUENCE: 31
aagcttctct gtgcagtcct tcatctgg                                        28

<210> SEQ ID NO 32
<211> LENGTH: 18
<212> TYPE: DNA
<213> ORGANISM: Artificial Sequence
<220> FEATURE:
<223> OTHER INFORMATION: synthetic polynucletodies

<400> SEQUENCE: 32
aagcttcagc ggggaaac                                                   18

<210> SEQ ID NO 33
<211> LENGTH: 18
<212> TYPE: DNA
<213> ORGANISM: Artificial Sequence
<220> FEATURE:
<223> OTHER INFORMATION: synthetic polynucletodies

<400> SEQUENCE: 33
ctcgagtaag tttgcctg                                                   18

<210> SEQ ID NO 34
<211> LENGTH: 40
<212> TYPE: DNA
<213> ORGANISM: Artificial Sequence
<220> FEATURE:
<223> OTHER INFORMATION: synthetic polynucletodies

<400> SEQUENCE: 34
ccatgggccc gttcgttaac aaacagttca actacaaaga                           40

<210> SEQ ID NO 35
<211> LENGTH: 33
<212> TYPE: DNA
<213> ORGANISM: Artificial Sequence
<220> FEATURE:
<223> OTHER INFORMATION: synthetic polynucletodies

<400> SEQUENCE: 35
aagctttttg ttgtagcctt tgtccaggga ttt                                  33

<210> SEQ ID NO 36
<211> LENGTH: 33
<212> TYPE: DNA
<213> ORGANISM: Artificial Sequence
<220> FEATURE:
<223> OTHER INFORMATION: synthetic polynucletodies

<400> SEQUENCE: 36
ctcgagtttg ttgtagcctt tgtccaggga ttt                                  33
```